(12) United States Patent
Feng et al.

(10) Patent No.: US 12,404,326 B2
(45) Date of Patent: Sep. 2, 2025

(54) BIVALENT BISPECIFIC ANTIBODY AND PREPARATION METHOD THEREOF, CODING GENE, HOST CELL AND COMPOSITION

(71) Applicant: CHANGCHUN GENESCIENCE PHARMACEUTICAL CO., LTD., Jilin (CN)

(72) Inventors: Xiao Feng, Jilin (CN); Lei Jin, Jilin (CN); Tao Wang, Jilin (CN); Hongrui Guo, Jilin (CN); Shuang Liu, Jilin (CN); Yuheng Chen, Jilin (CN); Ning Han, Jilin (CN); Yangqiu Liang, Jilin (CN)

(73) Assignee: CHANGCHUN GENESCIENCE PHARMACEUTICAL CO., LTD., Jilin (CN)

( * ) Notice: Subject to any disclaimer, the term of this patent is extended or adjusted under 35 U.S.C. 154(b) by 1102 days.

(21) Appl. No.: 17/418,856

(22) PCT Filed: Dec. 26, 2019

(86) PCT No.: PCT/CN2019/128582
§ 371 (c)(1),
(2) Date: Jun. 28, 2021

(87) PCT Pub. No.: WO2020/135555
PCT Pub. Date: Jul. 2, 2020

(65) Prior Publication Data
US 2022/0073610 A1    Mar. 10, 2022

(30) Foreign Application Priority Data

Dec. 28, 2018   (CN) .......................... 201811622069.2

(51) Int. Cl.
*C07K 16/28*   (2006.01)
(52) U.S. Cl.
CPC ...... *C07K 16/2803* (2013.01); *C07K 16/2827* (2013.01); *C07K 2317/24* (2013.01); *C07K 2317/31* (2013.01); *C07K 2317/35* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| 2004/0259156 A1* | 12/2004 | Zhu .......................... A61P 35/00 435/7.1 |
| 2009/0162359 A1 | 6/2009 | Klein et al. |
| 2012/0189541 A1 | 7/2012 | Wu |
| 2016/0222102 A1 | 8/2016 | Arndt et al. |
| 2017/0114151 A1 | 4/2017 | Dimasi et al. |
| 2019/0367633 A1 | 12/2019 | Liu et al. |
| 2020/0079869 A1 | 3/2020 | Feng et al. |
| 2020/0157185 A1 | 5/2020 | Gao et al. |

FOREIGN PATENT DOCUMENTS

| CN | 101821288 A | 9/2010 |
| CN | 101903404 A | 12/2010 |
| CN | 102586323 A | 7/2012 |
| CN | 104558193 A | 4/2015 |
| CN | 106084052 A | 11/2016 |
| CN | 107459578 A | 12/2017 |
| CN | 107759694 A | 3/2018 |
| CN | 108250296 A | 7/2018 |
| CN | 108640997 A | 10/2018 |
| CN | 108659112 A | 10/2018 |
| JP | 2010530756 A | 9/2010 |
| JP | 2013515509 A | 5/2013 |
| JP | 2014-504860 A | 2/2014 |
| JP | 2014-529600 A | 11/2014 |
| JP | 2014-533249 A | 12/2014 |
| JP | 2018505882 A | 3/2018 |
| WO | 9627011 A1 | 9/1996 |
| WO | 0177342 A1 | 10/2001 |
| WO | 2008157379 A2 | 12/2008 |

(Continued)

OTHER PUBLICATIONS

First Office Action dated Mar. 21, 2022 for Chinese patent application No. 201811622069.2, English translation provided by Google translate.

(Continued)

*Primary Examiner* — Daniel E Kolker
*Assistant Examiner* — Maureen Varina Driscoll
(74) *Attorney, Agent, or Firm* — Yue (Robert) Xu; Apex Attorneys at Law, LLP

(57) ABSTRACT

Provided are a bivalent bispecific antibody and a preparation method thereof, a coding gene, a host cell and a composition. The bivalent bispecific antibody comprises: a) a single-chain variable fragment scFv, a flexible peptide, a heavy chain IgG1 constant region CH1 and a hinge region partial sequence of the antibody that specifically binds to a first antigen, and b) a single-chain variable fragment scFv, and a light chain constant region CL, that is, scFv1-CL or CL-scFv1, of the antibody that specifically binds to a second antigen; or comprises: c) a light chain and a heavy chain of the antibody that specifically binds to the first antigen, and d) a light chain and a heavy chain of the antibody that specifically binds to the second antigen.

8 Claims, 4 Drawing Sheets
Specification includes a Sequence Listing.

(56) References Cited

FOREIGN PATENT DOCUMENTS

| WO | 2012018687 A1 | 2/2012 | | |
| WO | 2013/026839 A1 | 2/2013 | | |
| WO | WO-2013070565 A1 * | 5/2013 | ............ | A61P 31/04 |
| WO | 2017/055537 A1 | 4/2017 | | |
| WO | 2017/165464 A1 | 9/2017 | | |
| WO | 2018090950 A1 | 5/2018 | | |
| WO | WO-2019113464 A1 * | 6/2019 | ............ | C07K 14/71 |

OTHER PUBLICATIONS

Ulrich Brinkmann et al., "The making of bispecific antibodies", MABS, 2017, vol. 9, No. 2, 182-212.
Second Office Action dated Dec. 13, 2022 for Japanese patent application No. 2021-538377, English translation provided by Global Dossier.
First Office Action dated Jun. 29, 2021 for Chinese patent application No. 201811622069.2, English translation provided by Global Dossier.
K M Muller et al., "The first constant domain (C(H)1 and C(L)) of an antibody used as heterodimerization domain for bispecific miniantibodies",FEBS Letters 422(Jan. 30, 1998) 259-264.
First Office Action dated Jun. 21, 2022 for Japanese patent application No. 2021-538377, English translation provided by Global Dossier.
Partial European search report dated Aug. 5, 2022 for European patent application No. 19904064.3.
Zuo Zhuang et al:"An efficient route to the production of an IgG-like bispecific antibody", Protein Engineering, Oxford University Press, Surrey, GB, vol. 13, No. 5, May 1, 2000, pp. 361-367.
Lu D et al:"Simultaneous blockade of both the epidermal growth factor receptor and the insulin-like growth factor receptor signaling pathways in cancer cells with a fully human recombinant bispecific antibody", Journal of Biological Chemistry, American Society for Biochemistry and Molecular Biology, US, vol. 279, No. 4, Jan. 23, 2004, pp. 2856-2865.
International Search Report for PCT/CN2019/128582 mailed Mar. 27, 2020, ISA/CN.
Zhang Feng, et al., Development in Bispecific Antibody, Chinese Journal of Pharmaceutical Analysis, vol. 39, No. 1, Jan. 31, 2019.
Spiess C. et al., Alternative molecular formats and therapeutic applications for bispecific antibodies, Molecular Immunology, Dec. 31, 2015.
Shao Changli, et al., Prediction of three dimensional structure of bispecific antibodies linked by flexible peptide, Immunological Journal, vol. 25, No. 6, Nov. 30, 2009.
Fang Min, et al., The effect of interchain linker on the biological activity of single-chain bispecific antibodies, Chinese Science Bulletin, vol. 48, No. 18, Sep. 30, 2003.
Coloma, M.J., et al., Design and production of novel tetravalent bispecific antibodies, Nature Biotechnology, vol. 15, Feb. 1997.
Sherie L Morrison, A new design for bispecific antibodies enables efficient production of stable molecules with good pharmacodynamic properties, Nature Biotechnology, vol. 25 No. 11, Nov. 2007.
Philipp Holliger, et al., Engineered antibody fragments and the rise of single domains, Nature Biotechnology, vol. 23, No. 9, Sep. 2005.
Nicolas Fischer, et al., Bispecific Antibodies: Molecules That Enable Novel Therapeutic Strategies, Pathobiology, Jan. 2, 2007.
Juqun Shen, et al., Single variable domain antibody as a versatile building block for the construction of IgG-like bispecific antibodies, Journal of Immunological Methods, Oct. 26, 2006.
Chengbin Wu, et al., Simultaneous targeting of multiple disease mediators by a dual-variable-domain immunoglobulin, Nature Biotechnology, vol. 25 No. 11, Nov. 2007.
Milstein, C., et al., Hybrid hybridomas and their use in immunohistochemistry, Nature, vol. 305, Oct. 6, 1983.
Merchant, A.M., et al., An efficient route to human bispecific IgG, Nature Biotechnology, vol. 16, Jul. 1998.
Shane Atwell, et al., Stable Heterodimers from Remodeling the Domain Interface of a Homodimer using a Phage Display Library, J. Mol. Biol., 1997.
Jonathan H. Davis, et al., SEED bodies: fusion proteins based on strand-exchange engineered domain (SEED) CH3 heterodimers in an Fc analogue platform for asymmetric binders or immunofusions and bispecific antibodies, Protein Engineering, Design & Selection, vol. 23, No. 4, Feb. 4, 2010.
Michael J Gramer, et al., Production of stable bispecific IgG1 by controlled Fabarm exchange, mAbs, vol. 5 Issue 6, Aug. 22, 2013.
Wolfgang Schaefer, et al., Immunoglobulin domain crossover as a generic approach for the production of bispecific IgG antibodies, PNAS, vol. 108, No. 27, Jul. 5, 2011.
Patrick A. Baeuerle, et al., Bispecific T-Cell Engaging Antibodies for Cancer Therapy, American Association for Cancer Research, Jun. 2009.

* cited by examiner

SEQUENCE LISTING

<160> NUMBER OF SEQ ID NOS: 30

<210> SEQ ID NO 1
<211> LENGTH: 351
<212> TYPE: PRT
<213> ORGANISM: Artificial sequence
<220> FEATURE:
<223> OTHER INFORMATION: Heavy chain amino acid sequence

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Gln Val Gln Leu Val Gln Ser
            100                 105                 110

Gly Ala Glu Val Lys Lys Pro Gly Ala Ser Val Lys Val Ser Cys Lys
        115                 120                 125

Ala Ser Gly Tyr Thr Phe Thr Asn Tyr Val Leu His Trp Val Arg Gln
    130                 135                 140

Ala Pro Gly Gln Arg Leu Glu Trp Met Gly Tyr Phe Asn Pro Tyr Asn
145                 150                 155                 160

Asp Asp Ser Lys Tyr Asn Glu Lys Phe Lys Gly Arg Val Thr Ile Thr
                165                 170                 175

Arg Asp Thr Ser Ala Ser Thr Ala Tyr Met Glu Leu Ser Ser Leu Arg
            180                 185                 190

Ser Glu Asp Thr Ala Val Tyr Tyr Cys Ala Arg Gly Gly Tyr Tyr Ser
        195                 200                 205

```
Met Asp Tyr Trp Gly Gln Gly Thr Leu Val Thr Val Ser Ser Gly Gly
    210                 215                 220
Gly Gly Ser Gly Gly Gly Gly Ser Gly Gly Gly Ser Ala Ser Asp
225                 230                 235                 240
Ile Val Met Thr Gln Thr Pro Leu Ser Leu Pro Val Thr Pro Gly Gln
                245                 250                 255
Pro Ala Ser Ile Ser Cys Arg Ala Ser Gln Ser Leu Ala His Ser Asn
                260                 265                 270
Gly Tyr Thr Tyr Leu Gln Trp Tyr Leu Gln Lys Pro Gly Gln Ser Pro
            275                 280                 285
Gln Leu Leu Ile Tyr Lys Val Ser Lys Arg Phe Ser Gly Val Pro Asp
    290                 295                 300
Arg Phe Ser Gly Ser Gly Ser Gly Thr Asp Phe Thr Leu Lys Ile Ser
305                 310                 315                 320
Arg Val Glu Ala Glu Asp Val Gly Val Tyr Tyr Cys Ser Gln Ser Thr
                325                 330                 335
His Val Pro Tyr Thr Phe Gly Gln Gly Thr Lys Val Glu Ile Lys
                340                 345                 350

<210> SEQ ID NO 2
<211> LENGTH: 347
<212> TYPE: PRT
<213> ORGANISM: Artificial sequence
<220> FEATURE:
<223> OTHER INFORMATION: Heavy chain amino acid sequence

<400> SEQUENCE: 2

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Glu Val Gln Leu Val Glu Ser
            100                 105                 110
Gly Gly Gly Leu Val Gln Pro Gly Gly Ser Leu Arg Leu Ser Cys Ala
    115                 120                 125
Ala Ser Tyr Phe Pro Phe Ser Asp Ser Trp Ile His Trp Val Arg Gln
130                 135                 140
Ala Pro Gly Lys Gly Leu Glu Trp Val Ala Trp Ile Ser Pro Tyr Gly
                145                 150                 155                 160
Gly Ser Ser Tyr Tyr Ala Asp Ser Val Gln Asp Arg Phe Thr Ile Ser
                165                 170                 175
Ala Asp Thr Ser Lys Asn Thr Ala Tyr Leu Gln Met Asn Ser Leu Arg
            180                 185                 190
Ala Glu Asp Thr Ala Val Tyr Tyr Cys Ala Lys Arg His Trp Pro Gly
    195                 200                 205
Gly Phe Asp His Trp Gly Gln Gly Thr Leu Val Thr Val Ser Ser Gly
210                 215                 220
```

```
Gly Gly Gly Ser Gly Gly Gly Ser Gly Gly Gly Ser Ala Ser
225                 230                 235                 240

Asp Ile Gln Met Thr Gln Ser Pro Ser Ser Leu Ser Ala Ser Val Gly
                245                 250                 255

Asp Arg Val Thr Ile Thr Cys Ser Ala Ser Gln Asp Val Thr Thr Ala
            260                 265                 270

Val Ala Trp Tyr Gln Gln Lys Pro Gly Lys Ala Pro Lys Leu Leu Ile
        275                 280                 285

Tyr Ser Ala Ser Phe Pro Tyr Arg Gly Val Pro Ser Arg Phe Ser Gly
    290                 295                 300

Ser Gly Ser Gly Thr Asp Phe Thr Leu Thr Ile Ser Ser Leu Gln Pro
305                 310                 315                 320

Glu Asp Phe Ala Thr Tyr Tyr Cys Gln Gln Tyr Met Tyr His Pro Ser
                325                 330                 335

Thr Phe Gly Gln Gly Thr Lys Val Glu Ile Lys
                340                 345

<210> SEQ ID NO 3
<211> LENGTH: 347
<212> TYPE: PRT
<213> ORGANISM: Artificial sequence
<220> FEATURE:
<223> OTHER INFORMATION: Heavy chain amino acid sequence

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Tyr Phe Pro Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Ser Tyr Tyr Ala Asp Ser Val
    50                  55                  60

Gln Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Lys Arg His Trp Pro Gly Gly Phe Asp His Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Ser Asp Ile Gln Met Thr Gln Ser Pro Ser
    130                 135                 140

Ser Leu Ser Ala Ser Val Gly Asp Arg Val Thr Ile Thr Cys Ser Ala
145                 150                 155                 160

Ser Gln Asp Val Thr Thr Ala Val Ala Trp Tyr Gln Gln Lys Pro Gly
                165                 170                 175

Lys Ala Pro Lys Leu Leu Ile Tyr Ser Ala Ser Phe Pro Tyr Arg Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Tyr Met Tyr His Pro Ser Thr Phe Gly Gln Gly Thr Lys Val Glu
225                 230                 235                 240
```

```
Ile Lys Ala Ser Thr Lys Gly Pro Ser Val Phe Pro Leu Ala Pro Ser
            245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
            275                 280                 285

Thr Ser Gly Val His Thr Phe Pro Ala Val Leu Gln Ser Ser Gly Leu
            290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
            325                 330                 335

Asp Lys Lys Val Glu Pro Lys Ser Cys Asp Lys
            340                 345

<210> SEQ ID NO 4
<211> LENGTH: 351
<212> TYPE: PRT
<213> ORGANISM: Artificial sequence
<220> FEATURE:
<223> OTHER INFORMATION: Heavy chain amino acid sequence

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Leu His Trp Val Arg Gln Ala Pro Gly Gln Arg Leu Glu Trp Met
            35                  40                  45

Gly Tyr Phe Asn Pro Tyr Asn Asp Asp Ser Lys Tyr Asn Glu Lys Phe
        50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Gly Tyr Tyr Ser Met Asp Tyr Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Gly Ser Ala Ser Asp Ile Val Met Thr Gln Thr Pro Leu Ser
        130                 135                 140

Leu Pro Val Thr Pro Gly Gln Pro Ala Ser Ile Ser Cys Arg Ala Ser
145                 150                 155                 160

Gln Ser Leu Ala His Ser Asn Gly Tyr Thr Tyr Leu Gln Trp Tyr Leu
            165                 170                 175

Gln Lys Pro Gly Gln Ser Pro Gln Leu Leu Ile Tyr Lys Val Ser Lys
            180                 185                 190

Arg Phe Ser Gly Val Pro Asp Arg Phe Ser Gly Ser Gly Ser Gly Thr
            195                 200                 205

Asp Phe Thr Leu Lys Ile Ser Arg Val Glu Ala Glu Asp Val Gly Val
        210                 215                 220

Tyr Tyr Cys Ser Gln Ser Thr His Val Pro Tyr Thr Phe Gly Gln Gly
225                 230                 235                 240

Thr Lys Val Glu Ile Lys Ala Ser Thr Lys Gly Pro Ser Val Phe Pro
            245                 250                 255
```

Leu Ala Pro Ser Ser Lys Ser Thr Ser Gly Gly Thr Ala Ala Leu Gly
            260                 265                 270

Cys Leu Val Lys Asp Tyr Phe Pro Glu Pro Val Thr Val Ser Trp Asn
            275                 280                 285

Ser Gly Ala Leu Thr Ser Gly Val His Thr Phe Pro Ala Val Leu Gln
            290                 295                 300

Ser Ser Gly Leu Tyr Ser Leu Ser Ser Val Val Thr Val Pro Ser Ser
305                 310                 315                 320

Ser Leu Gly Thr Gln Thr Tyr Ile Cys Asn Val Asn His Lys Pro Ser
            325                 330                 335

Asn Thr Lys Val Asp Lys Lys Val Glu Pro Lys Ser Cys Asp Lys
            340                 345                 350

<210> SEQ ID NO 5
<211> LENGTH: 447
<212> TYPE: PRT
<213> ORGANISM: Artificial sequence
<220> FEATURE:
<223> OTHER INFORMATION: Heavy chain amino acid sequence

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Tyr Phe Pro Phe Ser Asp Ser
            20                  25                  30

Trp Ile His Trp Val Arg Gln Ala Pro Gly Lys Gly Leu Glu Trp Val
            35                  40                  45

Ala Trp Ile Ser Pro Tyr Gly Gly Ser Ser Tyr Tyr Ala Asp Ser Val
50                  55                  60

Gln Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Lys Arg His Trp Pro Gly Gly Phe Asp His Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Ser Cys
                355                 360                 365

Ala Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 6
<211> LENGTH: 352
<212> TYPE: PRT
<213> ORGANISM: Artificial sequence
<220> FEATURE:
<223> OTHER INFORMATION: Heavy chain amino acid sequence

<400> SEQUENCE: 6

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Asn Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Ser Glu Lys Phe
    50                  55                  60

Lys Gly Lys Ala Thr Leu Thr Ser Asp Lys Ser Ser Ile Thr Ala Tyr
65                  70                  75                  80

Met Glu Leu Ser Ser Leu Thr Ser Glu Asp Ser Ala Val Tyr Tyr Cys
                85                  90                  95

Ala Lys Gly Gly Leu Phe Thr Phe Asp Tyr Trp Gly Gln Gly Thr Thr
                100                 105                 110

Leu Thr Val Ser Ser Leu Gly Gly Cys Glu Pro Lys Ser Ser Asp Lys
            115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
                180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Asp Glu Leu Thr Lys Asn Gln Val Ser Leu Trp
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

<210> SEQ ID NO 7
<211> LENGTH: 360
<212> TYPE: PRT
<213> ORGANISM: Artificial sequence
<220> FEATURE:
<223> OTHER INFORMATION: Heavy chain amino acid sequence

<400> SEQUENCE: 7

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Asn Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Ser Glu Lys Phe
    50                  55                  60

Lys Gly Lys Ala Thr Leu Thr Ser Asp Lys Ser Ser Ile Thr Ala Tyr
65                  70                  75                  80

Met Glu Leu Ser Ser Leu Thr Ser Glu Asp Ser Ala Val Tyr Tyr Cys
                85                  90                  95

Ala Lys Gly Gly Leu Phe Thr Phe Asp Tyr Trp Gly Gln Gly Thr Thr
            100                 105                 110

Leu Thr Val Ser Ser Ser Gly Gly Gly Ser Ala Ser Leu Gly Gly
        115                 120                 125

Cys Glu Pro Lys Ser Ser Asp Lys Thr His Thr Cys Pro Pro Cys Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
                210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
                260                 265                 270

Thr Lys Asn Gln Val Ser Leu Trp Cys Leu Val Lys Gly Phe Tyr Pro
            275                 280                 285

Ser Asp Ile Ala Val Glu Trp Glu Ser Asn Gly Gln Pro Glu Asn Asn
            290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
                340                 345                 350

Lys Ser Leu Ser Leu Ser Pro Gly
            355                 360

<210> SEQ ID NO 8
<211> LENGTH: 369
<212> TYPE: PRT
<213> ORGANISM: Artificial sequence
<220> FEATURE:
<223> OTHER INFORMATION: Heavy chain amino acid sequence

<400> SEQUENCE: 8

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Asn Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Ser Glu Lys Phe
50                  55                  60

Lys Gly Lys Ala Thr Leu Thr Ser Asp Lys Ser Ser Ile Thr Ala Tyr
65                  70                  75                  80

Met Glu Leu Ser Ser Leu Thr Ser Glu Asp Ser Ala Val Tyr Tyr Cys
                85                  90                  95

Ala Lys Gly Gly Leu Phe Thr Phe Asp Tyr Trp Gly Gln Gly Thr Thr
                100                 105                 110

Leu Thr Val Ser Ser Gly Gly Gly Gly Ser Gly Gly Gly Gly Ser Gly
            115                 120                 125

Gly Gly Gly Ser Ala Ser Leu Gly Gly Cys Glu Pro Lys Ser Ser Asp
            130                 135                 140

Lys Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
                180                 185                 190

Asp Pro Glu Val Lys Phe Asn Trp Tyr Val Asp Gly Val Glu Val His
            195                 200                 205

```
Asn Ala Lys Thr Lys Pro Arg Glu Glu Gln Tyr Asn Ser Thr Tyr Arg
            210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Asp Glu Leu Thr Lys Asn Gln Val Ser Leu
        275                 280                 285

Trp Cys Leu Val Lys Gly Phe Tyr Pro Ser Asp Ile Ala Val Glu Trp
290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly

<210> SEQ ID NO 9
<211> LENGTH: 360
<212> TYPE: PRT
<213> ORGANISM: Artificial sequence
<220> FEATURE:
<223> OTHER INFORMATION: Heavy chain amino acid sequence

<400> SEQUENCE: 9

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Asn Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Ser Glu Lys Phe
50                  55                  60

Lys Gly Lys Ala Thr Leu Thr Ser Asp Lys Ser Ser Ile Thr Ala Tyr
65                  70                  75                  80

Met Glu Leu Ser Ser Leu Thr Ser Glu Asp Ser Ala Val Tyr Tyr Cys
                85                  90                  95

Ala Lys Gly Gly Leu Phe Thr Phe Asp Tyr Trp Gly Gln Gly Thr Thr
            100                 105                 110

Leu Thr Val Ser Ser Leu Gly Gly Cys Ser Gly Gly Gly Gly Ser Ala
        115                 120                 125

Ser Glu Pro Lys Ser Ser Asp Lys Thr His Thr Cys Pro Pro Cys Pro
130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190
```

```
Val Asp Gly Val Glu Val His Asn Ala Lys Thr Lys Pro Arg Glu Glu
            195                 200                 205

Gln Tyr Asn Ser Thr Tyr Arg Val Val Ser Val Leu Thr Val Leu His
        210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
            260                 265                 270

Thr Lys Asn Gln Val Ser Leu Trp Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly
        355                 360

<210> SEQ ID NO 10
<211> LENGTH: 349
<212> TYPE: PRT
<213> ORGANISM: Artificial sequence
<220> FEATURE:
<223> OTHER INFORMATION: Light chain amino acid sequence

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Tyr Phe Pro Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Ser Tyr Tyr Ala Asp Ser Val
    50                  55                  60

Gln Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Lys Arg His Trp Pro Gly Gly Phe Asp His Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Ala Ser Asp Ile Gln Met Thr Gln Ser Pro Ser
    130                 135                 140

Ser Leu Ser Ala Ser Val Gly Asp Arg Val Thr Ile Thr Cys Ser Ala
145                 150                 155                 160

Ser Gln Asp Val Thr Thr Ala Val Ala Trp Tyr Gln Gln Lys Pro Gly
                165                 170                 175

Lys Ala Pro Lys Leu Leu Ile Tyr Ser Ala Ser Phe Pro Tyr Arg Gly
            180                 185                 190
```

```
Val Pro Ser Arg Phe Ser Gly Ser Gly Ser Gly Thr Asp Phe Thr Leu
            195                 200                 205

Thr Ile Ser Ser Leu Gln Pro Glu Asp Phe Ala Thr Tyr Tyr Cys Gln
    210                 215                 220

Gln Tyr Met Tyr His Pro Ser Thr Phe Gly Gln Gly Thr Lys Val Glu
225                 230                 235                 240

Ile Lys Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
    275                 280                 285

Leu Gln Ser Gly Asn Ser Gln Glu Ser Val Thr Glu Gln Asp Ser Lys
290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345
```

<210> SEQ ID NO 11
<211> LENGTH: 353
<212> TYPE: PRT
<213> ORGANISM: Artificial sequence
<220> FEATURE:
<223> OTHER INFORMATION: Light chain amino acid sequence

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Leu His Trp Val Arg Gln Ala Pro Gly Gln Arg Leu Glu Trp Met
        35                  40                  45

Gly Tyr Phe Asn Pro Tyr Asn Asp Ser Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Ser Met Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Ala Ser Asp Ile Val Met Thr Gln Thr Pro Leu Ser
130                 135                 140

Leu Pro Val Thr Pro Gly Gln Pro Ala Ser Ile Ser Cys Arg Ala Ser
145                 150                 155                 160

Gln Ser Leu Ala His Ser Asn Gly Tyr Thr Tyr Leu Gln Trp Tyr Leu
                165                 170                 175

Gln Lys Pro Gly Gln Ser Pro Gln Leu Leu Ile Tyr Lys Val Ser Lys
            180                 185                 190

Arg Phe Ser Gly Val Pro Asp Arg Phe Ser Gly Ser Gly Ser Gly Thr
        195                 200                 205
```

```
Asp Phe Thr Leu Lys Ile Ser Arg Val Glu Ala Glu Asp Val Gly Val
210                 215                 220

Tyr Tyr Cys Ser Gln Ser Thr His Val Pro Tyr Thr Phe Gly Gln Gly
225                 230                 235                 240

Thr Lys Val Glu Ile Lys Arg Thr Val Ala Ala Pro Ser Val Phe Ile
                245                 250                 255

Phe Pro Pro Ser Asp Glu Gln Leu Lys Ser Gly Thr Ala Ser Val Val
                260                 265                 270

Cys Leu Leu Asn Asn Phe Tyr Pro Arg Glu Ala Lys Val Gln Trp Lys
                275                 280                 285

Val Asp Asn Ala Leu Gln Ser Gly Asn Ser Gln Glu Ser Val Thr Glu
290                 295                 300

Gln Asp Ser Lys Asp Ser Thr Tyr Ser Leu Ser Ser Thr Leu Thr Leu
305                 310                 315                 320

Ser Lys Ala Asp Tyr Glu Lys His Lys Val Tyr Ala Cys Glu Val Thr
                325                 330                 335

His Gln Gly Leu Ser Ser Pro Val Thr Lys Ser Phe Asn Arg Gly Glu
                340                 345                 350

Cys

<210> SEQ ID NO 12
<211> LENGTH: 353
<212> TYPE: PRT
<213> ORGANISM: Artificial sequence
<220> FEATURE:
<223> OTHER INFORMATION: Light chain amino acid sequence

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Gln Val Gln Leu Val
                100                 105                 110

Gln Ser Gly Ala Glu Val Lys Lys Pro Gly Ala Ser Val Lys Val Ser
                115                 120                 125

Cys Lys Ala Ser Gly Tyr Thr Phe Thr Asn Tyr Val Leu His Trp Val
130                 135                 140

Arg Gln Ala Pro Gly Gln Arg Leu Glu Trp Met Gly Tyr Phe Asn Pro
145                 150                 155                 160

Tyr Asn Asp Asp Ser Lys Tyr Asn Glu Lys Phe Lys Gly Arg Val Thr
                165                 170                 175

Ile Thr Arg Asp Thr Ser Ala Ser Thr Ala Tyr Met Glu Leu Ser Ser
                180                 185                 190

Leu Arg Ser Glu Asp Thr Ala Val Tyr Tyr Cys Ala Arg Gly Gly Tyr
                195                 200                 205

Tyr Ser Met Asp Tyr Trp Gly Gln Gly Thr Leu Val Thr Val Ser Ser
```

```
                        210                 215                 220

Gly Gly Gly Gly Ser Gly Gly Gly Ser Gly Gly Gly Ser Ala
225                 230                 235                 240

Ser Asp Ile Val Met Thr Gln Thr Pro Leu Ser Leu Pro Val Thr Pro
                245                 250                 255

Gly Gln Pro Ala Ser Ile Ser Cys Arg Ala Ser Gln Ser Leu Ala His
                260                 265                 270

Ser Asn Gly Tyr Thr Tyr Leu Gln Trp Tyr Leu Gln Lys Pro Gly Gln
            275                 280                 285

Ser Pro Gln Leu Leu Ile Tyr Lys Val Ser Lys Arg Phe Ser Gly Val
        290                 295                 300

Pro Asp Arg Phe Ser Gly Ser Gly Ser Gly Thr Asp Phe Thr Leu Lys
305                 310                 315                 320

Ile Ser Arg Val Glu Ala Glu Asp Val Gly Val Tyr Tyr Cys Ser Gln
                325                 330                 335

Ser Thr His Val Pro Tyr Thr Phe Gly Gln Gly Thr Lys Val Glu Ile
                340                 345                 350

Lys

<210> SEQ ID NO 13
<211> LENGTH: 349
<212> TYPE: PRT
<213> ORGANISM: Artificial sequence
<220> FEATURE:
<223> OTHER INFORMATION: Light chain amino acid sequence

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Glu Val Gln Leu Val
            100                 105                 110

Glu Ser Gly Gly Gly Leu Val Gln Pro Gly Gly Ser Leu Arg Leu Ser
        115                 120                 125

Cys Ala Ala Ser Tyr Phe Pro Phe Ser Asp Ser Trp Ile His Trp Val
    130                 135                 140

Arg Gln Ala Pro Gly Lys Gly Leu Glu Trp Val Ala Trp Ile Ser Pro
145                 150                 155                 160

Tyr Gly Gly Ser Ser Tyr Tyr Ala Asp Ser Val Gln Asp Arg Phe Thr
                165                 170                 175

Ile Ser Ala Asp Thr Ser Lys Asn Thr Ala Tyr Leu Gln Met Asn Ser
            180                 185                 190

Leu Arg Ala Glu Asp Thr Ala Val Tyr Tyr Cys Ala Lys Arg His Trp
        195                 200                 205

Pro Gly Gly Phe Asp His Trp Gly Gln Gly Thr Leu Val Thr Val Ser
    210                 215                 220
```

```
Ser Gly Gly Gly Gly Ser Gly Gly Gly Ser Gly Gly Gly Ser
225                 230                 235                 240

Ala Ser Asp Ile Gln Met Thr Gln Ser Pro Ser Ser Leu Ser Ala Ser
                245                 250                 255

Val Gly Asp Arg Val Thr Ile Thr Cys Ser Ala Ser Gln Asp Val Thr
            260                 265                 270

Thr Ala Val Ala Trp Tyr Gln Gln Lys Pro Gly Lys Ala Pro Lys Leu
        275                 280                 285

Leu Ile Tyr Ser Ala Ser Phe Pro Tyr Arg Gly Val Pro Ser Arg Phe
    290                 295                 300

Ser Gly Ser Gly Ser Gly Thr Asp Phe Thr Leu Thr Ile Ser Ser Leu
305                 310                 315                 320

Gln Pro Glu Asp Phe Ala Thr Tyr Tyr Cys Gln Gln Tyr Met Tyr His
                325                 330                 335

Pro Ser Thr Phe Gly Gln Gly Thr Lys Val Glu Ile Lys
            340                 345
```

<210> SEQ ID NO 14
<211> LENGTH: 214
<212> TYPE: PRT
<213> ORGANISM: Artificial sequence
<220> FEATURE:
<223> OTHER INFORMATION: Light chain amino acid sequence

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Pro Tyr Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr His Pro Ser
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 15

```
<211> LENGTH: 116
<212> TYPE: PRT
<213> ORGANISM: Artificial sequence
<220> FEATURE:
<223> OTHER INFORMATION: Light chain amino acid sequence

<400> SEQUENCE: 15
```

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Lys Gly Asn Thr Tyr Leu His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

Leu Gly Gly Cys
        115

```
<210> SEQ ID NO 16
<211> LENGTH: 124
<212> TYPE: PRT
<213> ORGANISM: Artificial sequence
<220> FEATURE:
<223> OTHER INFORMATION: Light chain amino acid sequence

<400> SEQUENCE: 16
```

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Lys Gly Asn Thr Tyr Leu His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

Ser Gly Gly Gly Gly Ser Ala Ser Leu Gly Gly Cys
        115                 120

```
<210> SEQ ID NO 17
<211> LENGTH: 133
<212> TYPE: PRT
<213> ORGANISM: Artificial sequence
<220> FEATURE:
<223> OTHER INFORMATION: Light chain amino acid sequence

<400> SEQUENCE: 17
```

Asp Val Val Met Thr Gln Thr Pro Leu Ser Leu Pro Val Ser Leu Gly
1               5                   10                  15

```
Asp Gln Ala Ser Ile Ser Cys Arg Ser Ser Gln Ser Leu Val His Ser
            20                  25                  30

Lys Gly Asn Thr Tyr Leu His Trp Tyr Leu Gln Lys Pro Gly Gln Ser
         35                  40                  45

Pro Lys Leu Leu Ile Tyr Arg Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
            100                 105                 110

Gly Gly Gly Gly Ser Gly Gly Gly Gly Ser Gly Gly Gly Gly Ser Ala
            115                 120                 125

Ser Leu Gly Gly Cys
        130

<210> SEQ ID NO 18
<211> LENGTH: 112
<212> TYPE: PRT
<213> ORGANISM: Artificial sequence
<220> FEATURE:
<223> OTHER INFORMATION: VL

<400> SEQUENCE: 18

Asp Ile Val Met Thr Gln Thr Pro Leu Ser Leu Pro Val Thr Pro Gly
 1               5                  10                  15

Gln Pro Ala Ser Ile Ser Cys Arg Ala Ser Gln Ser Leu Ala His Ser
            20                  25                  30

Asn Gly Tyr Thr Tyr Leu Gln Trp Tyr Leu Gln Lys Pro Gly Gln Ser
         35                  40                  45

Pro Gln Leu Leu Ile Tyr Lys Val Ser Lys Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Tyr Thr Phe Gly Gln Gly Thr Lys Val Glu Ile Lys
            100                 105                 110

<210> SEQ ID NO 19
<211> LENGTH: 117
<212> TYPE: PRT
<213> ORGANISM: Artificial sequence
<220> FEATURE:
<223> OTHER INFORMATION: VH

<400> SEQUENCE: 19

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Val Leu His Trp Val Arg Gln Ala Pro Gly Gln Arg Leu Glu Trp Met
         35                  40                  45

Gly Tyr Phe Asn Pro Tyr Asn Asp Asp Ser Lys Tyr Asn Glu Lys Phe
     50                  55                  60

Lys Gly Arg Val Thr Ile Thr Arg Asp Thr Ser Ala Ser Thr Ala Tyr
 65                  70                  75                  80
```

-continued

Met Glu Leu Ser Ser Leu Arg Ser Glu Asp Thr Ala Val Tyr Tyr Cys
                85                  90                  95

Ala Arg Gly Gly Tyr Tyr Ser Met Asp Tyr Trp Gly Gln Gly Thr Leu
            100                 105                 110

Val Thr Val Ser Ser
        115

<210> SEQ ID NO 20
<211> LENGTH: 107
<212> TYPE: PRT
<213> ORGANISM: Artificial sequence
<220> FEATURE:
<223> OTHER INFORMATION: VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Pro Tyr Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr His Pro Ser
                85                  90                  95

Thr Phe Gly Gln Gly Thr Lys Val Glu Ile Lys
            100                 105

<210> SEQ ID NO 21
<211> LENGTH: 118
<212> TYPE: PRT
<213> ORGANISM: Artificial sequence
<220> FEATURE:
<223> OTHER INFORMATION: VH

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Tyr Phe Pro Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Ser Tyr Tyr Ala Asp Ser Val
    50                  55                  60

Gln Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Lys Arg His Trp Pro Gly Gly Phe Asp His Trp Gly Gln Gly Thr
            100                 105                 110

Leu Val Thr Val Ser Ser
        115

<210> SEQ ID NO 22
<211> LENGTH: 454
<212> TYPE: PRT

<213> ORGANISM: Artificial sequence
<220> FEATURE:
<223> OTHER INFORMATION: Human PD-L1-mFc

<400> SEQUENCE: 22

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr Ser Gly Gly
    210                 215                 220

Gly Gly Ser Val Pro Arg Asp Cys Gly Cys Lys Pro Cys Ile Cys Thr
225                 230                 235                 240

Val Pro Glu Val Ser Ser Val Phe Ile Phe Pro Pro Lys Pro Lys Asp
                245                 250                 255

Val Leu Thr Ile Thr Leu Thr Pro Lys Val Thr Cys Val Val Val Asp
            260                 265                 270

Ile Ser Lys Asp Asp Pro Glu Val Gln Phe Ser Trp Phe Val Asp Asp
        275                 280                 285

Val Glu Val His Thr Ala Gln Thr Gln Pro Arg Glu Glu Gln Phe Asn
    290                 295                 300

Ser Thr Phe Arg Ser Val Ser Glu Leu Pro Ile Met His Gln Asp Trp
305                 310                 315                 320

Leu Asn Gly Lys Glu Phe Lys Cys Arg Val Asn Ser Ala Ala Phe Pro
                325                 330                 335

Ala Pro Ile Glu Lys Thr Ile Ser Lys Thr Lys Gly Arg Pro Lys Ala
            340                 345                 350

Pro Gln Val Tyr Thr Ile Pro Pro Lys Glu Gln Met Ala Lys Asp
        355                 360                 365

Lys Val Ser Leu Thr Cys Met Ile Thr Asp Phe Phe Pro Glu Asp Ile
370                 375                 380

Thr Val Glu Trp Gln Trp Asn Gly Gln Pro Ala Glu Asn Tyr Lys Asn
```

```
                385                 390                 395                 400
        Thr Gln Pro Ile Met Asp Thr Asp Gly Ser Tyr Phe Val Tyr Ser Lys
                        405                 410                 415
        Leu Asn Val Gln Lys Ser Asn Trp Glu Ala Gly Asn Thr Phe Thr Cys
                        420                 425                 430
        Ser Val Leu His Glu Gly Leu His Asn His Thr Glu Lys Ser Leu
                        435                 440                 445
        Ser His Ser Pro Gly Lys
                        450

<210> SEQ ID NO 23
<211> LENGTH: 134
<212> TYPE: PRT
<213> ORGANISM: Artificial sequence
<220> FEATURE:
<223> OTHER INFORMATION: Human CD47-His

<400> SEQUENCE: 23

Gln Leu Leu Phe Asn Lys Thr Lys Ser Val Glu Phe Thr Phe Cys Asn
1               5                   10                  15
Asp Thr Val Val Ile Pro Cys Phe Val Thr Asn Met Glu Ala Gln Asn
                20                  25                  30
Thr Thr Glu Val Tyr Val Lys Trp Lys Phe Lys Gly Arg Asp Ile Tyr
            35                  40                  45
Thr Phe Asp Gly Ala Leu Asn Lys Ser Thr Val Pro Thr Asp Phe Ser
        50                  55                  60
Ser Ala Lys Ile Glu Val Ser Gln Leu Leu Lys Gly Asp Ala Ser Leu
65                  70                  75                  80
Lys Met Asp Lys Ser Asp Ala Val Ser His Thr Gly Asn Tyr Thr Cys
                85                  90                  95
Glu Val Thr Glu Leu Thr Arg Glu Gly Glu Thr Ile Ile Glu Leu Lys
            100                 105                 110
Tyr Arg Val Val Ser Trp Phe Ser Pro Ser Gly Gly Gly Gly Ser His
        115                 120                 125
His His His His His
    130

<210> SEQ ID NO 24
<211> LENGTH: 7
<212> TYPE: PRT
<213> ORGANISM: Artificial sequence
<220> FEATURE:
<223> OTHER INFORMATION: IgG1 partial hinge region

<400> SEQUENCE: 24

Glu Pro Lys Ser Cys Asp Lys
1               5

<210> SEQ ID NO 25
<211> LENGTH: 5
<212> TYPE: PRT
<213> ORGANISM: Artificial Sequence
<220> FEATURE:
<223> OTHER INFORMATION: Flexible peptide

<400> SEQUENCE: 25

Gly Gly Gly Gly Ser
1               5

<210> SEQ ID NO 26
```

```
<211> LENGTH: 7
<212> TYPE: PRT
<213> ORGANISM: Artificial Sequence
<220> FEATURE:
<223> OTHER INFORMATION: Flexible peptide

<400> SEQUENCE: 26

Gly Gly Gly Gly Ser Ala Ser
1               5

<210> SEQ ID NO 27
<211> LENGTH: 4
<212> TYPE: PRT
<213> ORGANISM: Artificial Sequence
<220> FEATURE:
<223> OTHER INFORMATION: Linker

<400> SEQUENCE: 27

Leu Gly Gly Cys
1

<210> SEQ ID NO 28
<211> LENGTH: 4
<212> TYPE: PRT
<213> ORGANISM: Artificial Sequence
<220> FEATURE:
<223> OTHER INFORMATION: Linker

<400> SEQUENCE: 28

Gly Gly Gly Cys
1

<210> SEQ ID NO 29
<211> LENGTH: 15
<212> TYPE: PRT
<213> ORGANISM: Artificial Sequence
<220> FEATURE:
<223> OTHER INFORMATION: Flexible peptide

<400> SEQUENCE: 29

Gly Gly Gly Gly Ser Gly Gly Gly Gly Ser Gly Gly Gly Gly Ser
1               5                   10                  15

<210> SEQ ID NO 30
<211> LENGTH: 21
<212> TYPE: PRT
<213> ORGANISM: Artificial Sequence
<220> FEATURE:
<223> OTHER INFORMATION: Flexible peptide

<400> SEQUENCE: 30

Gly Gly Gly Gly Ser Ala Ser Gly Gly Gly Gly Ser Ala Ser Gly Gly
1               5                   10                  15
Gly Gly Ser Ala Ser
            20
```

BIVALENT BISPECIFIC ANTIBODY AND PREPARATION METHOD THEREOF, CODING GENE, HOST CELL AND COMPOSITION

CROSS REFERENCE TO RELATED APPLICATIONS

This application is a US National Phase application based upon PCT Application No. PCT/CN2019/128582, filed Dec. 26, 2019, which claims the priority of Chinese Patent Application No. 201811622069.2, filed to China National Intellectual Property Administration on Dec. 28, 2018, and titled with "BIVALENT BISPECIFIC ANTIBODY AND PREPARATION METHOD THEREOF, CODING GENE, HOST CELL AND COMPOSITION", and the disclosures of which are hereby incorporated by reference.

SEQUENCE LISTING

This application contains references to amino acid sequences and/or nucleic acid sequences which have been submitted concurrently herewith as the sequence listing text file entitled "69427904_210033-APXU-GENSCI-Sequence_listing-v,", file size S6,643 bytes, created on Mar. 5, 2025. The aforementioned sequence listing is hereby incorporated by reference in its entirety.

FIELD

The present disclosure relates to the technical field of antibody medicine, specifically to a bivalent bispecific antibody and preparation method thereof, coding gene, host cell and composition.

BACKGROUND

A bispecific monoclonal antibody (BsAb) is a special antibody that is artificially made to bind two different antigens at the same time. Bispecific antibodies can recognize both tumor target cells and immune effector cells, so they have dual functions of antibody specificity and mediating the cytotoxicity of effector cells. Bispecific antibodies can recruit effector cells at tumor sites and activate effector cells to exert anti-tumor effects. The mechanism of killing tumor cells mediated by bispecific antibodies includes cell proliferation, cytokine release, cytotoxic peptides and regulation of enzymes. In vivo and clinical studies have proved that bispecific antibody-mediated immunotherapy can treat tumors in some animals, and clinically can mitigate the condition of patients with tumor and prolong their life. Therefore, the application of bispecific antibody-mediated immunocompetent cells in tumor therapy has a good prospect.

Bispecific antibodies are not nature products and can only be prepared artificially. Bi- or multi-specific antibodies in the art can bind to at least two antigens and can be produced by cell fusion, chemical conjugation or recombinant DNA technology. Recently, a wide variety of recombinant bispecific antibody structures have been developed, such as tetravalent bispecific antibodies by fusion of, for example, an IgG antibody and a single-chain domain (Coloma, M. J., et al., Nature Biotech. 15 (1997) 159-163; WO2001077342; and Morrison, S. L., Nature Biotech. 25 (2007) 1233-1234). In addition, many other new forms that can bind to more than two antigens have been developed, in which the main structure of the antibody (IgA, IgD, IgE, IgG or IgM) is no longer limited to, such as diabodies, triabodies or tetrabodies, minibodies and several single-chain forms (scFv, BisscFv) (Holliger, P., et al., Nature Biotech. 23 (2005) 1126-1136; Fischer, N., and Léger, O., Pathobiology 74 (2007) 3-14; Shen, J., et al., Journal of Immunogical Methods 318 (2007) 65-74; Wu, C., et al., Nature Biotech. 25 (2007) 1290-1297).

In one method, the cell quadroma technology (Milstein, C. and A. C. Cuello, Nature, 305 (1983) 537-40) is utilized to produce a bispecific antibody that is very similar to a natural antibody. The cell quadroma technology is based on the somatic fusion of two different hybridoma cell lines expressing murine monoclonal antibodies with the desired bispecific antibody specificity. Because of the random pairing of two different heavy and light chains of antibodies in the hybridoma cell lines, up to 10 different antibody types will be generated, of which only one is the desired functional bispecific antibody. Due to the presence of mismatched by-products and significantly low yields, complicated purification procedures are required (Morrison, S. L., Nature Biotech 25 (2007) 1233-1234). Generally, if recombinant expression technology is used, the same problem of mismatch by-products still exists.

A method used to avoid the problem of mismatch by-products is called "knobs-into-holes". The purpose is to force the heavy chains from two different antibodies to pair with each other by introducing mutation into the CH3 domain to modify the contact interface. In one chain, amino acids with large volume are replaced by amino acids with short side chains to form a "hole". Conversely, amino acids with a large side chain are introduced to the other CH3 domain to form a "knob". By co-expressing these two heavy chains, a higher yield of heterodimer form ("knob-hole") compared with homodimer form ("hole-hole" or "knob-knob") was observed (Ridgway, J. B., Presta, L. G., Carter, P. and WO 1996027011). The percentage of heterodimer can be further increased by reconstruction of the interaction interface of the two CH3 domains using phage display method and introduction of disulfide bonds to stabilize the heterodimer (Merchant, A. M., et al., Nature Biotech 16 (1998) 677-681; Atwell, S., Ridgway, J. B., Wells, J. A., Carter, P., J. Mol. Biol. 270 (1997) 26-35). An important constraint of this strategy is that the light chains of the two parent antibodies must be the same to prevent mismatches and formation of inactive molecules.

In addition to the "knob-hole" structure, the Fc pairing of different half-antibodies can also be achieved through the strand-exchange engineered domain (SEED) technology of IgG and IgA CH3 (Davis, J. H., et al., Protein Eng. Des. Sel., 2010, 23 (4): 195-202).

In order to solve the problem of the incorrect assembly of different light chains, a new process of double-cell line expressing half-antibodies separately and in vitro assembly has been developed recently. Inspired by the half-antibody random exchange process of human IgG4 antibodies naturally occurring under physiological conditions, GenMab has developed FAE (Fab-arm exchange) bifunctional antibody technology (Gramer, M. J., et al., MAbs 2013, 5 (6): 962-973.). Introducing two point mutations, K409R and F405L, into the IgG1 heavy chain CH3 domains of the two target antibodies respectively, can produce half-antibody exchange rearrangement similar to that of IgG4 antibodies. Two different IgG1 antibodies after mutation were expressed in two CHO cell lines respectively, and the assembly between the light and heavy chains of each half-antibody was completed. After protein A affinity purification, precise assembly between heterogeneous half-antibodies can be achieved in vitro by using a mild oxidant system.

In addition to sharing light chains with the same sequence or performing in vitro assembly, the correct assembly of light chains of antibodies can also be facilitated by Crossmab technology. A representative product is Roche's Ang-2/VEGF CrossMab CH1-CL. Based on the modification of "knobs-into-holes", Crossmab technology exchanged CL and CH1 in the Fab domain of Ang-2 antibody and remained the Fab domain of VEGF antibody unchanged. The light chain of the modified Ang-2 antibody is not easily mismatched with the heavy chain of the VEGF antibody, and the "knob-hole" structure can promote the heterodimerization of the two heavy chains (Schaefer, W, et al., Proc Natl. Acad. Sci. USA, 2011, 108 (27): 11187-11192).

Moreover, two single-chain antibodies (scFv) or two Fabs can be linked through a peptide to form a bifunctional antibody fragment. A representative product is BiTE (bispecific T-cell engager) series products developed by Micromet in German. This series of products is generated by linking anti-CD3 single-chain antibodies with the single-chain antibodies against different anti-tumor cell surface antigens through a peptide (Baeuerle, P. A., et al., Cancer Res., 2009, 69 (12): 4941-4944). The advantage of such antibody structure is that it has a small molecular weight, can be expressed in prokaryotic cells, and does not require the consideration of incorrect assembly; while the disadvantage is that it cannot mediate some corresponding biological functions due to a lack of antibody Fc fragment, and its half-life is short.

The patent application publications US2015/0284475A1 and CN101896504A disclose bivalent bispecific antibodies, but the bivalent bispecific antibodies in the two applications have low affinity for antigens. The flexible peptide disclosed in "Prediction of three dimensional structure of bispecific antibodies linked by flexible peptide" published by Shao Changli, was used to modify the bivalent bispecific antibodies in the two aforementioned applications, but the affinity of the antibodies was still not ideal.

In view of the problems of light chain mismatches, low correct assembly rate of light and heavy chains, and the too large or small molecule size of the above-mentioned bispecific antibodies, it is necessary to develop a new type of a bivalent bispecific antibody.

SUMMARY

In view of this, the present disclosure provides a bivalent bispecific antibody and a preparation method thereof, a coding gene, a host cell and a composition. The antibody has a less mismatched assembly rate of light and heavy chains and a moderate molecular size.

In order to achieve the above objects of the present disclosure, the present disclosure provides the following technical solutions:

The present disclosure provides a bivalent bispecific antibody, comprising
  a) a single-chain variable fragment (scFv) derived from an antibody that specifically binds to a first antigen, a flexible peptide, a heavy chain constant region CH1 and a partial hinge region of IgG1, namely CH1-partial hinge-linker (flexible peptide)-scFv2 or scFv2-linker-CH1-partial hinge, and
  b) a single-chain variable fragment (scFv) derived from an antibody that specifically binds to a second antigen and a light chain constant region CL, namely scFv1-CL or CL-scFv1;

or comprising
  c) a light chain and a heavy chain of an antibody that specifically binds to a first antigen, and
  d) a light chain and a heavy chain of an antibody that specifically binds to a second antigen, wherein light chain variable region of the light chain is linked to a flexible peptide and a linker, and heavy chain variable region of the heavy chain is linked to a heavy chain Fc fragment through a flexible peptide and a linker.

Preferably, the flexible peptide comprises a sequence of (G4S/G4SAS) n, wherein n is an integer greater than or equal to 0, and the IgG1 partial hinge region linked to the flexible peptide comprises a sequence of EPKSCDK (SEQ ID NO: 24), wherein (G4S/G4SAS) n represents (GGGGS (SEQ ID NO: 25)) n_or (GGGGSAS (SEQ ID NO: 26)) n, and n is an integer greater than or equal to 0.

The linker comprises a sequence of L/GGGC (L/GGGC represents LGGC (SEQ ID NO: 27) or GGGC (SEQ ID NO: 28)), and the first cysteine residue (C) in heavy chain hinge region linked to the linker is mutated to serine(S).

Preferably, in steps a) and b), CL and CH1 form a heterodimer via a disulfide bond between the terminal cysteine residue in CL and the cysteine residue in the heavy chain hinge region.

Preferably, in steps c) and d), the terminal cysteine residue in the linker LGGC (SEQ ID NO: 27) or GGGC (SEQ ID NO: 28) linked to the heavy chain and the terminal cysteine residue in the linker LGGC (SEQ ID NO: 27) or GGGC (SEQ ID NO: 28) linked to the light chain form a disulfide bond; and the CH3 domain of first heavy chain and the CH3 domain of second heavy chain are modified to a structure that facilitates the formation of the bivalent bispecific antibody.

Preferably, the modification comprises
  a) modification to the CH3 domain of the first heavy chain: in the interface between the CH3 domain of the first heavy chain and the CH3 domain of the second heavy chain of the bivalent bispecific antibody, an amino acid residue in the CH3 domain of the first heavy chain is replaced with an amino acid residue with a volume larger than the original amino acid residue to form a knob in the CH3 domain of the first heavy chain, wherein the knob is capable of inserting into a hole of the CH3 domain of the second heavy chain, and
  b) modification to the CH3 domain of the second heavy chain: in the interface between the CH3 domain of the second heavy chain and the CH3 domain of the first heavy chain of the bivalent bispecific antibody, an amino acid residue in the CH3 domain of the second heavy chain is replaced with an amino acid residue with a volume smaller than the original amino acid residue to form a hole in the CH3 domain of the second heavy chain, wherein the hole is capable of holding the knob of the CH3 domain of the first heavy chain;
  wherein each of the first heavy chain variable region and the light chain variable region is linked to (GGGGS (SEQ ID NO: 25)) n_or (GGGGSAS (SEQ ID NO: 26)) n and LGGC (SEQ ID NO: 27) or GGGC (SEQ ID NO: 28), and a disulfide bond is formed between the cysteine residues of the two L/GGGC.

Preferably, the amino acid residue with a volume larger than the original amino acid residue is selected from the group consisting of arginine (R), phenylalanine (P), tyrosine (Y), and tryptophan (W).

The amino acid residue with a volume smaller than the original amino acid residue is selected from the group consisting of alanine (A), serine(S), threonine (T), and valine (V).

Preferably, the bivalent bispecific antibody provided by the present disclosure comprises:
 a) a single-chain variable fragment (scFv), a flexible peptide, a heavy chain constant region CH1 and a partial hinge region of IgG1, derived from an antibody that specifically binds to a first antigen, i.e., the amino acid sequence as shown in SEQ ID NO: 2, and
 b) a single-chain variable fragment (scFv) and a light chain constant region CL derived from an antibody that specifically binds to a second antigen, i.e., the amino acid sequence as shown in SEQ ID NO: 11;
or comprises
 c) a light chain and a heavy chain of an antibody that specifically binds to a first antigen, i.e., the amino acid sequences as shown in SEQ ID NO: 5 and SEQ ID NO: 14, and
 d) a light chain and a heavy chain of an antibody that specifically binds to a second antigen, i.e., the amino acid sequences as shown in SEQ ID NO: 6 and SEQ ID NO: 15, wherein the light chain variable region is linked to a flexible peptide and a linker, and the heavy chain variable region is linked to the heavy chain Fc fragment through a flexible peptide and a linker.

The present disclosure also provides a method for producing the bivalent bispecific antibody, comprising the following steps:
 a) Transforming a host cell with the following vectors:
  a first vector (comprising the gene encoding SEQ ID NO: 2), comprising a nucleic acid encoding a single-chain variable fragment and a heavy chain constant region CH1 of an antibody that specifically binds to a first antigen, and
  a second vector (comprising the gene encoding SEQ ID NO: 11), comprising a nucleic acid encoding a single-chain variable fragment and a light chain constant region of an antibody that specifically binds to a second antigen;
 or with the following vectors:
  a third vector (comprising the gene encoding SEQ ID NO: 14), comprising a nucleic acid encoding a light chain of an antibody that specifically binds to a first antigen,
  a fourth vector (comprising the gene encoding SEQ ID NO: 5), comprising a nucleic acid encoding a heavy chain of an antibody that specifically binds to a first antigen,
  a fifth vector (comprising the gene encoding SEQ ID NO: 15), comprising a nucleic acid encoding a light chain of an antibody that specifically binds to a second antigen, wherein the light chain variable region is linked to a linker, and
  a sixth vector (comprising the gene encoding SEQ ID NO: 6), comprising a nucleic acid encoding a heavy chain of an antibody that specifically binds to a second antigen, wherein the heavy chain variable region is linked to the heavy chain Fc fragment through a linker;
 b) culturing the host cell under conditions that allow the synthesis of an antibody; and
 c) recovering the antibody from the culture.

The present disclosure also provides a nucleic acid molecule encoding the bivalent bispecific antibody of the present disclosure, comprising
 a first nucleic acid (the gene encoding SEQ ID NO: 2), encoding a single-chain variable fragment (scfv), a flexible peptide, a heavy chain igg1 constant region CH1, and a partial hinge region of an antibody that specifically binds to a first antigen, and
 a second nucleic acid (the gene encoding SEQ ID NO: 11), encoding a single-chain variable fragment (scfv) and a light chain constant region CL of an antibody that specifically binds to a second antigen;
or comprising
 a third nucleic acid (the gene encoding SEQ ID NO: 14), encoding a light chain of an antibody that specifically binds to a first antigen,
 a fourth nucleic acid (the gene encoding SEQ ID NO: 5), encoding a heavy chain of an antibody that specifically binds to a first antigen,
 a fifth nucleic acid (the gene encoding SEQ ID NO: 15), encoding a light chain of an antibody that specifically binds to a second antigen, wherein the light chain variable region is linked to a flexible peptide and a linker, and
 a sixth nucleic acid (the gene encoding SEQ ID NO: 6), encoding a heavy chain of an antibody that specifically binds to a second antigen, wherein the heavy chain variable region is linked to the heavy chain Fc fragment through a flexible peptide and a linker.

The present disclosure also provides a host cell, comprising
 a first vector, comprising a nucleic acid encoding a single-chain variable fragment and a heavy chain constant region CH1 of an antibody that specifically binds to a first antigen, and
 a second vector, comprising a nucleic acid encoding a single-chain variable fragment and a light chain constant region of an antibody that specifically binds to a second antigen;
or comprising
 a third vector, comprising a nucleic acid encoding a light chain of an antibody that specifically binds to a first antigen,
 a fourth vector, comprising a nucleic acid encoding a heavy chain of an antibody that specifically binds to a first antigen,
 a fifth vector, comprising a nucleic acid encoding a light chain of an antibody that specifically binds to a second antigen, wherein the light chain variable region is linked to a linker, and
 a sixth vector, comprising a nucleic acid encoding a heavy chain of an antibody that specifically binds to a second antigen, wherein the heavy chain variable region is linked to the heavy chain Fc fragment through a linker.

The present disclosure also provides a composition comprising the bivalent bispecific antibody, and the composition is a pharmaceutical composition or a diagnostic composition.

Preferably, the pharmaceutical composition also comprises at least one pharmaceutical excipient.

The present disclosure provides a bivalent bispecific antibody and a preparation method thereof, a coding gene, a host cell and a composition. The bivalent bispecific antibody comprises a) a single-chain variable fragment (scFv), a flexible peptide, a heavy chain constant region CH1 and a partial hinge region of IgG1, derived from an antibody that specifically binds to a first antigen, namely CH1-partial hinge-linker (flexible peptide)-scFv2 or scFv2-linker-CH1-partial hinge, and b) a single-chain variable fragment (scFv) and a light chain constant region CL derived from an antibody that specifically binds to a second antigen, namely scFv1-CL or CL-scFv1;

or comprises c) a light chain and a heavy chain of an antibody that specifically binds to a first antigen, and d) a light chain and a heavy chain of an antibody that specifically binds to a second antigen, wherein light chain variable region of the light chain is linked to a flexible peptide and a linker, and heavy chain variable region of the heavy chain is linked to the heavy chain Fc fragment through a flexible peptide and a linker.

The present disclosure has the following technical effects.

The bivalent bispecific antibody of the present disclosure has high affinities to the first antigen molecule and the second antigen molecule, which are equivalent to the parent monoclonal antibody molecule. For example, the affinities of B2 and FV1 to PD-L1 are 1.09E-10 M and 2.71E-10 M respectively; and the affinities of B2 and FV1 to PD-L1 are 2.58E-8 M and 1.50E-8 M, respectively. It can be seen that the antibody of the present disclosure has a high correct assembly rate of light and heavy chains and a moderate molecular size.

DETAILED DESCRIPTION

Figure 1:
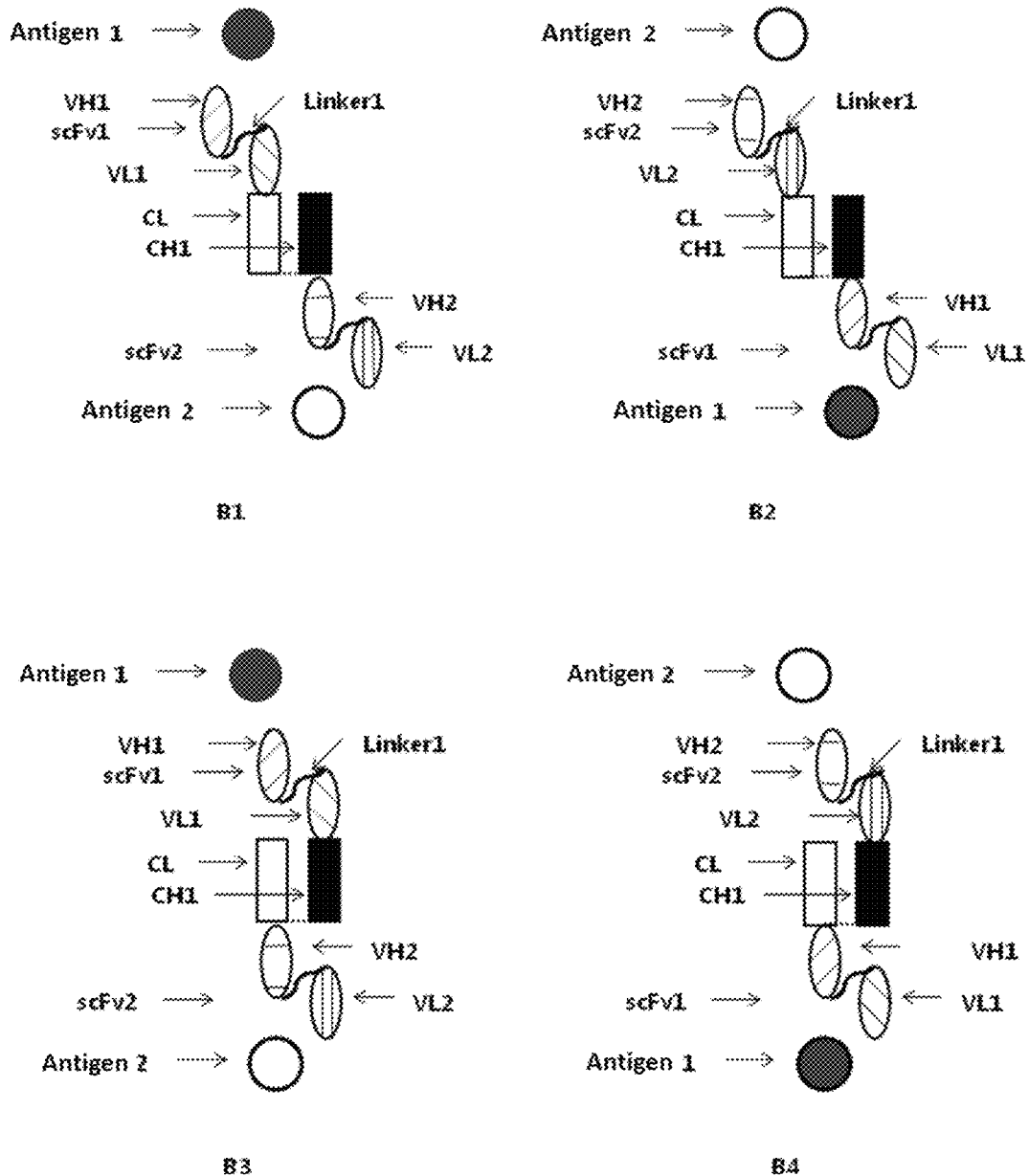
FIG. 1 is a schematic diagram of bivalent bispecific antibodies with B structure, including four structures: B1, B2, B3 and B4.

The present disclosure discloses a bivalent bispecific antibody and a preparation method thereof, a coding gene, a host cell and a composition. In view of the content herein, those skilled in the art can make appropriate modifications to the process parameters. It should be particularly indicated that, all similar replacements and changes are obvious for those skilled in the art, which are deemed to be included in the present disclosure. The methods and uses of the present disclosure have been described by way of preferred embodiments, and it will be apparent to those skilled in the art that changes as well as appropriate modifications and combinations of the methods and uses described herein may be made without departing from the content, spirit and scope of the present disclosure, to achieve and apply the techniques of the present disclosure.

The terms used herein are explained as follows.

The term "antibody" used herein refers to an intact, monoclonal antibody. The antibody comprises two pairs of "light chain" (LC) and "heavy chain" (HC). The light chain and heavy chain of the antibody are polypeptides composed of several domains. In an intact antibody, each heavy chain comprises a heavy chain variable region VH and a heavy chain constant region. The heavy chain constant region includes the heavy chain constant domains CH1, CH2, and CH3 (antibody types IgA, IgD, and IgG) and optionally the heavy chain constant domain CH4 (antibody types IgE and IgM). Each light chain comprises a light chain variable region VL and a light chain constant region CL. An example of naturally occurring intact antibodies are the IgG antibodies. The variable regions VH and VL can be further divided into hypervariable regions, called complementarity determining regions (CDRs), and there are regions distributed between CDR which are more conservative, called framework regions (FRs). Each VH and VL consists of three CDRs and four FRs, arranged from the amino terminal to the carboxy terminal in the following order: FR1, CDR1, FR2, CDR2, FR3, CDR3, and FR4 (Janeway, C. A., Jr., et al., (2001) Immunobiology, 5th edition, Garland Press; and Woof, J., Burton D. Nat. Rev. Immunol. 4 (2004) 89-99). The two pairs of heavy and light chains can specifically bind to the same antigen. Therefore, the intact antibody is a bivalent, monospecific antibody. The "antibody" includes, for example, mouse antibodies, human antibodies, chimeric antibodies, humanized antibodies, and genetically engineered antibodies, provided that their unique properties are maintained. The particularly preferred antibodies are human or humanized antibodies, especially recombinant human or humanized antibodies.

There are five types of mammalian antibody heavy chain, represented by Greek letters: a, δ, ε, γ, and u (Janeway, C. A., Jr. et al., (2001) Immunobiology, 5th edition, Garland Press). The type of heavy chain corresponds to the type of antibody, and these chains are present in IgA, IgD, IgE, IgG, and IgM antibodies, respectively (Rhoades, R. A., Pflanzer, RG. (2002), Human Physiology, 4th edition, Thommesen knowledge). Different heavy chains differ in size and composition. The heavy chains a and y contain about 450 amino acids, while u and & contain about 550 amino acids.

Each heavy chain has two types of region, the constant region and the variable region. The constant region is the same in all antibodies of the same isotype, but different in antibodies of different isotypes. The heavy chains y, a and δ have a constant region composed of three constant domains CH1, CH2 and CH3 and a hinge region for increasing flexibility (Woof, J., Burton D. Nat. Rev. Immunol. 4 (2004) 89-99). The heavy chains u and & have a constant region composed of 4 constant domains CH1, CH2, CH3 and CH4 (Janeway, C. A., Jr. et al., (2001) Immunobiology, 5th edition, published by Garland Society). The variable region of the heavy chain differs in antibodies produced by different B cells, but is the same for all antibodies produced by a single B cell or B cell clone. The variable region of each heavy chain is approximately 110 amino acids in length and consists of a single antibody domain.

In mammals, there are only two types of light chains, which are called 2 and K. The light chain comprises two continuous domains: one constant domain CL and one variable domain VL. The light chain is approximate 211-217 amino acids in length. Preferably, the light chain is a κ light chain, and the constant domain CL is preferably CK.

The term "monoclonal antibody" or "monoclonal antibody composition" used herein refers to an antibody preparation of a single amino acid composition.

The "antibody" according to the present disclosure can be of any type (such as IgA, IgD, IgE, IgG and IgM, preferably IgG or IgE), or subtype (such as IgG1, IgG2, IgG3, IgG4, IgA1 and IgA2, preferably IgG1). The bivalent bispecific antibody according to the present disclosure is derived from two antibodies with the Fc fragments which are of the same subtype (such as IgG1, IgG4, etc., preferably IgG1), preferably Fc fragments of the same allotype.

The "Fc fragment of an antibody" or "Fc fragment" is a term well known to those skilled in the art and is defined based on the papain cleavage of the antibody. The antibody according to the present disclosure comprises, for example, Fc fragment, preferably the Fc fragment derived from a human antibody and preferably all other parts of a human constant region. The Fc fragment of the antibody is directly involved in complement activation, Clq binding, C3 activation and Fc receptor binding. Although the effect of the antibody on the complement system depends on certain conditions, the binding to Clq is caused by the binding sites in the Fc fragment. The binding sites are prior art and described in, for example, Lukas, T. J., et al., J. Immunol. 127 (1981) 2555-2560; Brunhouse, Cebra, J. J., Mo 1. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP0307434. The binding sites are, for example, L234, L235, D270, N297, E318, K320, K322, P331 and P329 (according to Kabat's EU catalog number). Antibodies of subtypes IgG1, IgG2, and IgG3 usually exhibit complement activation, Clq binding and C3 activation, while IgG4 neither activates the complement system, nor binds to Clq or activates C3. Preferably, the Fc fragment is a human Fc fragment.

As used herein, the term "recombinant human antibody" includes all human antibodies prepared, expressed, produced or isolated by recombinant methods, such as antibodies isolated from host cells, such as from NSO or CHO cells, or isolated from human immunoglobulin genes of transgenic animal, or antibodies expressed by recombinant expression vectors transfected into host cells. This recombinant human antibody has constant and variable regions in a rearranged form.

As used herein, a "variable domain" refers to each pair of light chain and heavy chain that directly participates in the binding of an antibody to an antigen. The domains of human variable light chain and heavy chain have the same general structure and each domain comprises four framework regions (FR), which have generally conserved sequence and connected by three hypervariable regions (CDRs). The framework region adopts a self-folding conformation and the CDR can form a loop connecting the self-folding structure. The CDRs in each chain are maintained in their three-dimensional structure by the framework regions and form an antigen binding site together with the CDRs from the other chain. The CDR3 regions of heavy chain and light chain of antibody play a particularly important role in the binding specificity/affinity of the antibodies of the present disclosure.

As used herein, the term "hypervariable region" or "antigen-binding fragment of an antibody" refers to amino acid residues of the antibody that are responsible for antigen binding. The hypervariable region comprises amino acid residues from the "complementarity determining region". "Framework regions" are those regions of variable domains other than the hypervariable region residues defined herein. Therefore, the light chain and heavy chain of the antibody from N-terminal to C-terminal include the domains FR1, CDR1, FR2, CDR2, FR3, CDR3, and FR4, and the CDRs on each chain are separated by the framework amino acids. In particular, CDR3 of the heavy chain is the most conducive region for antigen binding. The CDR and FR regions are determined according to the standard definition of Kabat et al., Sequences of Proteins of Immunological Interest, 5th edition, Public Health Service, National Institutes of Health, Bethesda, MD, (1991).

The "constant regions" of the heavy and light chains do not directly participate in the binding of antibodies to antigens but exhibit multiple effector functions.

As used herein, the term "bivalent bispecific antibody" refers to an antibody as described above, in which two single-chain variable fragments specifically bind to different antigens, that is, the first single-chain variable fragment and the light chain constant region specifically bind to the first antigen, while the second single-chain variable fragment and the heavy chain constant region 1 and partial hinge region specifically bind to the second antigen. The bivalent bispecific antibody can specifically bind to two different antigens but no more than two antigens at the same time. In contrast, on one hand, a monospecific antibody that can only bind to one antigen, and on the other hand, a tetravalent, tetraspecific antibody that can bind four antigen at the same time.

As used herein, the terms "antigen" and "antigen molecule" are used interchangeably and refer to all molecules that can be specifically bound by an antibody. The bivalent bispecific antibody specifically binds to a first antigen and a second different antigen. As used herein, the term "antigen" includes, for example, proteins, different epitopes on the protein (as different antigens within the meaning of the present disclosure), and polysaccharides, which mainly includes bacteria, viruses and parts of other microorganisms (shell, envelope, cell wall, flagella, fimbriae and toxins). Lipids and nucleic acids are antigenic only when combined with proteins and polysaccharides. Non-microbial exogenous (non-self) antigens may include pollen, egg white, and proteins from transplanted tissues and organs or proteins on the surface of infused blood cells. Preferably, the antigen is selected from the group consisting of cytokines, cell surface proteins, enzymes and receptor.

Tumor antigens are those antigens contained in MHC I or MHC II molecules on the surface of tumor cells. These antigens can sometimes be presented by tumor cells, and never by normal cells. As such, they are called tumor-specific antigens (TSAs) and are typically produced by tumor-specific mutations. More common are antigens presented by tumor cells and normal cells, and they are called tumor-associated antigens (TAAs). Cytotoxic T lymphocytes that recognize these antigens may be able to destroy tumor cells before they proliferate or metastasize. Tumor antigens can also be present on the tumor surface in the form of, for example, mutant receptors, in which case they should be recognized by B cells.

In a preferred embodiment, at least one of the two different antigens (the first and second antigens) to which the bivalent bispecific antibody specifically binds is a tumor antigen.

In another preferred embodiment, both of the two different antigens (the first and second antigens) to which the bivalent bispecific antibody specifically binds are tumor antigens. In this case, the first and second antigens may also be the two different epitopes on the same tumor-specific protein.

In another preferred embodiment, one of the two different antigens (the first and second antigens) to which the bivalent bispecific antibody specifically binds is a tumor antigen, and the other is an effector cell antigen, such as a T cell receptor, CD3, CD16, etc.

In another preferred embodiment, one of the two different antigens (the first and second antigens) to which the bivalent bispecific antibody specifically binds is a tumor antigen, and the other is an anti-cancer substance such as a toxin or a kinase inhibitor.

As used herein, "specific binding" or "specifically bind" refers to an antibody that specifically binds to an antigen. Preferably, the binding affinity of the antibody that specifically binds to the antigen has a KD value below 10-9 mol/L, such as 10-10 mol/L, preferably a KD value below 10-10 mol/L, such as 10-12 mol/L. Binding affinity is determined using standard binding assays, such as surface plasmon resonance technology (Biacore).

The term "epitope" comprises any polypeptide determinant capable of specifically binding an antibody. In certain embodiments, epitope determinants include chemically polar surface groupings of molecules, such as amino acids, sugar side chains, phosphoryl or sulfonyl groups. In certain embodiments, an epitope can have specific three-dimensional structural characteristics and/or specific charging characteristics. An epitope is a region of an antigen bound by an antibody. In certain embodiments, when an antibody preferably recognizes its target antigen in a complex mixture of proteins and/or macromolecules, the antibody is said to specifically bind to the antigen.

As used herein, the term "nucleic acid" or "nucleic acid molecule" includes DNA molecules and RNA molecules. The nucleic acid molecule may be single-stranded or double-stranded, but is preferably double-stranded DNA.

As used herein, the expressions "cell", "cell line" and "cell culture" are used interchangeably, and all of these include progeny. Therefore, the terms "transformant" and "transformed cells" include primary subject cells and cultures derived therefrom, regardless of the number of generation. It is also understood that the DNA content of all offspring may not be exactly the same due to intentional or unintentional mutations. They also include the mutant offspring with the same function or biological activity screened in the originally transformed cells. When different names are meant, it will be clear due to the context.

As used herein, the term "transformation" refers to the process of transferring a vector/nucleic acid into a host cell. If cells without an insurmountable cell wall barrier are used as host cells, transfection is performed, for example, by the calcium phosphate precipitation method as described in Graham and van der Eh, Virology 52 (1978) 546ff. However, other methods of introducing DNA into cells can also be used, such as by nuclear injection or by protoplast fusion. If prokaryotic cells or cells containing substantial cell wall structures are used, transfection is performed, for example, by calcium treatment with calcium oxide, as described in Cohen, F. N., et al., PNAS. 69 (1972) 7110ff.

The use of transformation recombination to generate antibodies is well known in the prior art and is described in, for example, the review article Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., et al., Arzneimittel Forschung 48 (1998) 870-880 and U.S. Pat. Nos. 6,331,415 and 4,816,567.

As used herein, "expression" refers to the process of transcribing nucleic acid into mRNA and/or the process of subsequently translating the transcribed mRNA into peptides, polypeptides or proteins. The transcript and the encoded polypeptide are collectively called the gene product. If the polynucleotide is derived from genomic DNA, expression in eukaryotic cells may include splicing of mRNA.

A "vector" is a nucleic acid molecule, especially self-replicating one, which transfers the inserted nucleic acid molecule into and/or between host cells. The term includes vectors whose primary function is to insert DNA or RNA into cells, replication vectors whose primary function is to replicate DNA or RNA, and expression vectors whose function is to transcribe and/or translate DNA or RNA. It also includes vectors that provide more than one of the above-mentioned functions.

An "expression vector" is a polynucleotide, which can be transcribed and translated into a polypeptide after being introduced into a suitable host cell. "Expression system" generally refers to a suitable host cell including an expression vector whose function is to produce a desired expression product.

The bivalent bispecific antibody according to the present disclosure is preferably produced by a recombinant method. The method is generally known in the art and includes protein expression in prokaryotic and eukaryotic cells, subsequent isolation of antibody polypeptides and generally purification to pharmaceutical purity. For protein expression, nucleic acids encoding light and heavy chains or fragments thereof are inserted in an expression vector by standard methods. The expression is carried out in suitable prokaryotic or eukaryotic host cells such as CHO cells, NSO cells, SP2/0 cells, HEK293 cells, COS cells, yeast or *E. coli* cells, and the antibody is recovered from the cells (the supernatant or cells after lysis). The bivalent bispecific antibody may exist in whole cells, as cell lysates, or in partially purified or substantially pure form. Purification is carried out by standard techniques, including alkali/SDS treatment, column chromatography and other techniques well known in the art to eliminate other cellular components or other contaminants, such as other cellular nucleic acids or proteins. Reference could be made to Ausubel, F., et al., Current Protocols in Molecular Biology, Greene Publishing and WileyInter science, New York (1987). The expression in NSO cells is described in, for example, Barnes, L. M., et al., Cytotechnology 32 (2000) 109-123; and Barnes, L. M., et al., Biotech. Bioeng. 73 (2001) 261-270. Transient expression is described in, for example, Durocher, Y., et al., Nucl. Acids Res. 30 (2002) IV. The cloning of variable domains is described in Orlando, R., et al., Proc. Natl. Acad. Sci. USA 86 (1989) 3833-3837; Carter, P., et al., Proc. Natl. Acad. Sci. USA 89 (1992) 4285-4289; and Norderha, L., et al., J. Immunol. Methods 204 (1997) 77-87. A preferred transient expression system (HEK 293) is described in Schlaeger, E. J., and Christensen, K., Cytotechnology 30 (1999) 71-83 and Schlaeger, E. J., J. Immunol. Methods 194 (1996) 191-199.

Control sequences suitable for prokaryotes comprise, for example, promoters, optional operon sequences, and ribosome binding sites. It is known that eukaryotic cells utilize promoters, enhancers and polyadenylation signals.

A nucleic acid is "operably linked" when placed in a functional relationship with another nucleic acid sequence. For example, the DNA of the polypeptide is operably linked to a leader sequence or a DNA secreting leader sequence, provided that it is expressed as a preprotein involved in the secretion of the polypeptide; the coding sequence is operably linked to a promoter or enhancer, provided that it affects the transcription of the sequence; or the coding sequence is operably linked to a ribosome binding site, provided that it is positioned to facilitate translation. Generally, "operably linked" means that the DNA sequence being linked is continuous, and in the case of being linked to sequence secreting a leader, is continuous and in an open reading frame. However, the enhancer does not have to be continuous. Linkage is achieved by linking at convenient restriction sites. If the site is not present, the synthetic oligonucleotide adaptor or linker is used according to conventional practice.

By conventional immunoglobulin purification procedures, such as, for example, protein A-agarose, hydroxyapatite chromatography, gel electrophoresis, dialysis, or affinity chromatography, the bivalent bispecific antibody will be appropriately isolated from the culture medium. The DNA and RNA encoding monoclonal antibodies can be easily isolated and sequenced using conventional procedures. Quadroma cells can function as the source of the DNA and RNA. Once isolated, the DNA can be inserted into an expression vector, which is then transfected into host cells that would otherwise not produce immunoglobulin, such as HEK293 cells, CHO cells, or myeloma cells, to generate the recombinant monoclonal antibodies in the host cells.

Amino acid sequence variants (or mutants) of bivalent bispecific antibodies are prepared by introducing appropriate nucleotide changes into the antibody DNA, or by nucleotide synthesis. However, such modification can only be performed in a very limited range, such as the range described above. In addition, the modification does not change the above-mentioned antibody characteristics, such as IgG isotype and antigen binding, but can improve the yield of recombinant products or protein stability or promote purification.

Raw materials or reagents, used in the bivalent bispecific antibody and the preparation method thereof, the coding gene, host cell and composition provided by the present disclosure, can all be purchased from the market.

The present disclosure will be further illustrated by the following examples:

Example 1 Preparation of Bivalent Bispecific Antibodies

1. Construction of transient transfection expression vectors for bivalent bispecific antibodies (1) Materials The sequence of VL (SEQ ID NO: 18) and the sequence of VH (SEQ ID NO: 19) are derived from the anti-human CD47 humanized monoclonal antibody 059-4.16.2 H1L2, which was obtained by humanization of murine antibody (CN 201610436519.3) obtained from quadromas.

The sequence of VL (SEQ ID NO: 20) and the sequence of VH (SEQ ID NO: 21) was derived from the anti-human PD-L1 humanized monoclonal antibody 047 Ab-6, which was obtained by panning the natural human antibodies library (CN 201810044303.1). The coding nucleotides of heavy chain constant region CH1, hinge region and Fc of IgG1, and nucleotides of Kappa chain constant region are derived from human IgG1.

Figure 2:
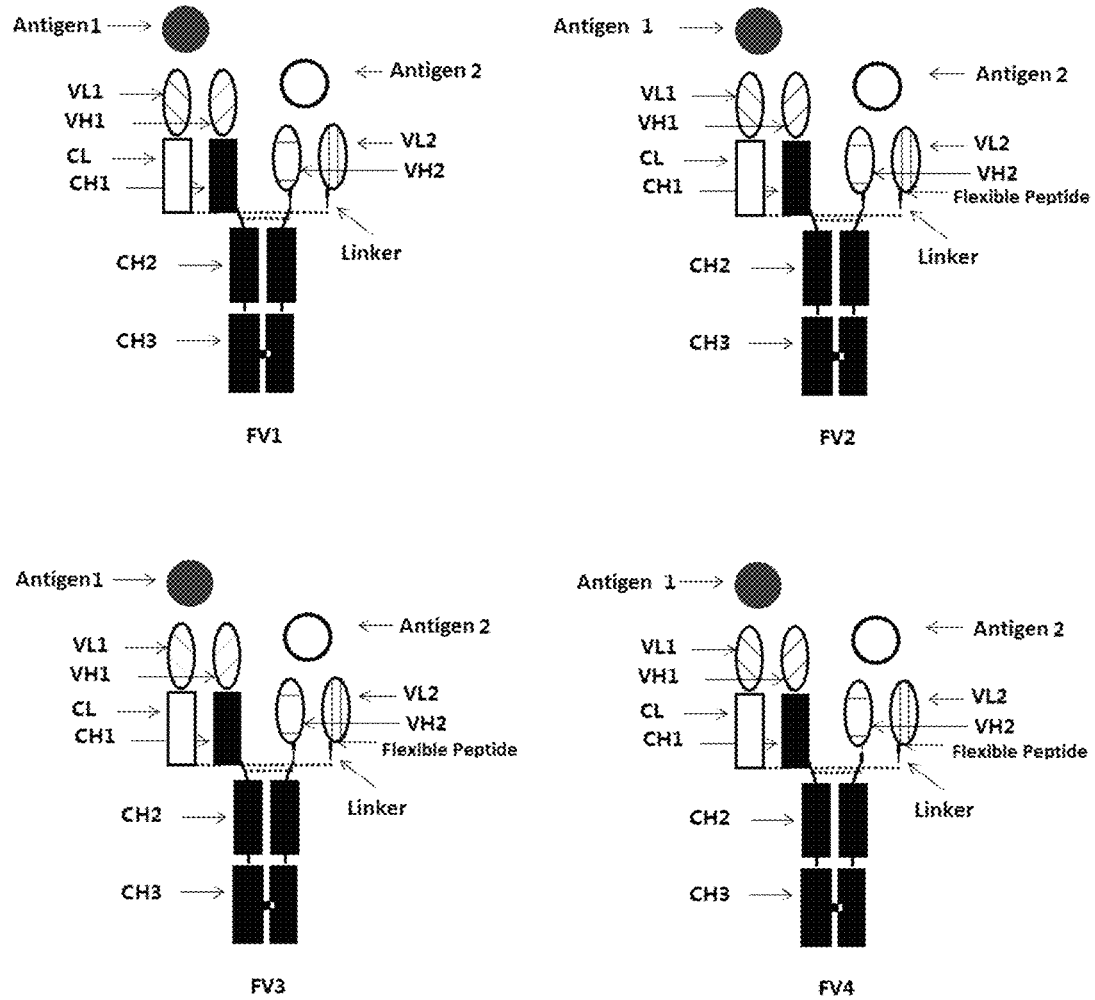
FIG. 2 is a schematic diagram of bivalent bispecific antibodies with FV structure, including four structures: FV1, FV2, FV3 and FV4. In the structure FV1, there is no flexible peptide; in the structure FV2, the sequence of the flexible peptide is GGGGS (SEQ ID NO: 25) or GGGGSAS (SEQ ID NO: 26); in the structure FV3, the sequence of the flexible peptide is GGGGSGGGGSGGGGS (SEQ ID NO: 29) or GGGGSASGGGGSASGGGGSAS (SEQ ID NO: 30); and in the structure FV4, the sequence of the flexible peptide is GGGGS (SEQ ID NO: 25) or GGGGSAS (SEQ ID NO: 26).

(2) Methods pGS003 was selected to construct the expression vectors for the heavy chain and light chain of bivalent bispecific antibodies (8 antibodies, the schematic diagrams of the structure are shown in FIG. 1 and FIG. 2). Primers were designed according to the coding nucleotides of VL and VH derived from the anti-human CD47 humanized monoclonal antibody 059-4.16.2 H1L2, the coding nucleotides of VL and VH derived from the anti-human PD-L1 humanized monoclonal antibody 047 Ab-6, the coding nucleotides of heavy chain constant region CH1, hinge region and Fc of IgG1, and nucleotide sequence of Kappa chain constant region, and multiple cloning sites in the vector. After PCR amplification, 9 heavy chain coding sequences and 8 light chain coding sequences were respectively cloned into pGS003 by in vitro recombination method (Synbio Technologies, iMulli Multi-fragment Recombination Cloning Kit), as shown in Table 1. After sequencing to identify the correct insertion of the antibody gene, the recombinant expression vector was transformed into E. coli TOP10F'. Then single colonies was picked and inoculated in LB medium containing 100 μg/mL of ampicillin, and cultured with shaking at 37° C. for 16 hours. The plasmids were extracted using endotoxin-removal, large-scale extraction kit of Zymo Research, and the obtained plasmids were dissolved in 1 mL of ultrapure water, and the plasmid concentration and OD260/280 were determined with a spectrophotometer. A plasmid with OD260/280 value between 1.8 and 1.9 is relatively pure plasmid DNA.

TABLE 1

List of transient transfection expression vectors for heavy and light chains

| Heavy chain expression vector | Heavy chain amino acid sequence | Light chain expression vector | Light chain amino acid sequence |
|---|---|---|---|
| H1 | SEQ ID NO: 1 | L1 | SEQ ID NO: 10 |
| H2 | SEQ ID NO: 2 | L2 | SEQ ID NO: 11 |
| H3 | SEQ ID NO: 3 | L3 | SEQ ID NO: 12 |
| H4 | SEQ ID NO: 4 | L4 | SEQ ID NO: 13 |
| H5 | SEQ ID NO: 5 | L5 | SEQ ID NO: 14 |
| H6 | SEQ ID NO: 6 | L6 | SEQ ID NO: 15 |
| H7 | SEQ ID NO: 7 | L7 | SEQ ID NO: 16 |
| H8 | SEQ ID NO: 8 | L8 | SEQ ID NO: 17 |
| H9 | SEQ ID NO: 9 | / | / |

2. Transfection, Expression and Detection in Mammalian 293E Cells

In the above 9 heavy chain expression vectors and 8 light chain expression vectors, H1, L2, L3 and H4 were used to express scFv of anti-hCD47, L1, H2, H3 and L4 were used to express scFv of anti-hPD-L1, H5 and L5 were used to express VH and VL of anti-hPD-L1, respectively, H6, H7, H8 and H9 were used to express VH of anti-hCD47, and L6, L7 and L8 were used to express VL of anti-hCD47.

Figure 3:
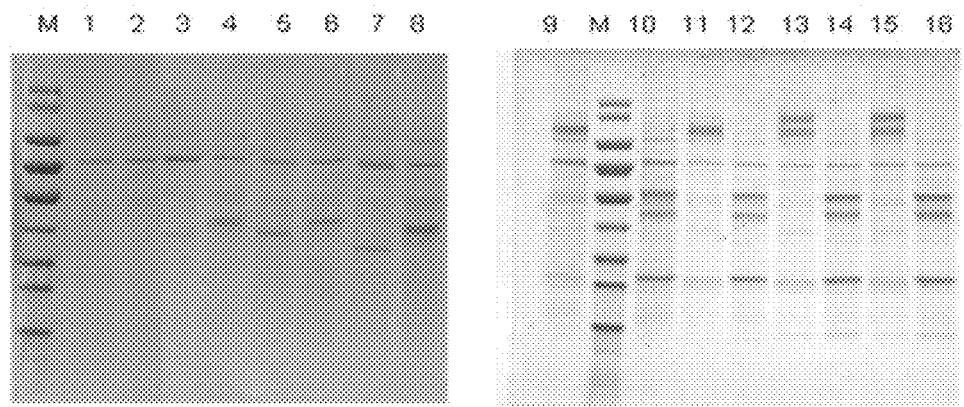
FIG. 3 shows the SDS-PAGE results of the transient expression of bispecific antibodies with B structure and with FV structure. M indicates Marker; Lanes 1, 3, 5, 7, 9, 11, 13, and 15 represent the non-reducing electrophoresis results of B1, B2, B3, B4, FV1, FV2, FV3, and FV4, respectively; and Lanes 2, 4, 6, 8, 10, 12, 14, and 16 represent the reducing electrophoresis results of B1, B2, B3, B4, FV1, FV2, FV3 and FV4, respectively.
Figure 4:
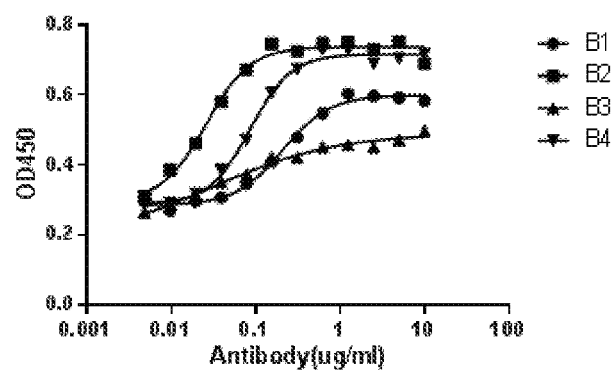
FIG. 4 shows the ELISA results of bivalent bispecific antibodies with B structure and with FV structure, including the ELISA results of four B structures of B1, B2, B3 and B4 (FIG. 4A) and four FV structures of FV1, FV2, FV3 and FV4 (FIG. 4B).
Figure 4:
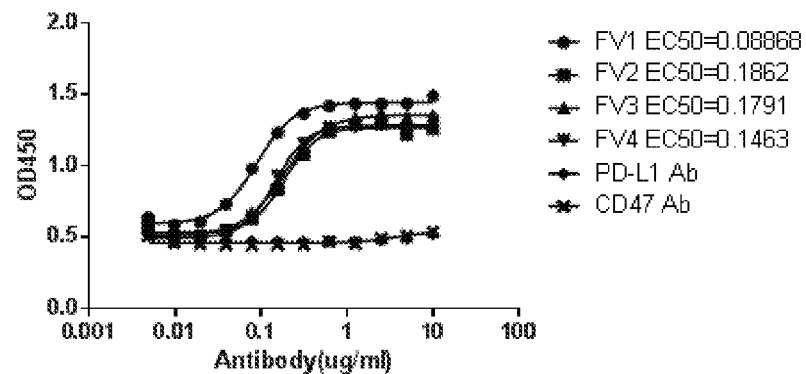

After combining the above vectors in accordance with H1+L1 (B1 structure), H2+L2 (B2 structure), H3+L3 (B3 structure), H4+L4 (B4 structure), H5+L5+H6+L6 (FV1 structure), H5+L5+H7+L7 (FV2 structure), H5+L5+H8+L8 (FV3 structure) and H5+L5+H9+L7 (FV4 structure), 2 mL 293E system of transient transfection expression was performed for evaluation. As to flexible peptide and linker, FV1 was L/GGGC (LGGC (SEQ ID NO: 27) or GGGC (SEQ ID NO: 28)), FV2 was GGGGS (SEQ ID NO: 25) or GGGG-SAS (SEQ ID NO: 26)+LGGC (SEQ ID NO: 27) or GGGC (SEQ ID NO: 28), FV3 was GGGGSGGGGSGGGGS (SEQ ID NO: 29) or GGGGSASGGGGSASGGGGSAS (SEQ ID NO: 30)+LGGC (SEQ ID NO: 27) or GGGC (SEQ ID NO: 28), and for FV4, the light chain was GGGGS (SEQ ID NO: 25) or GGGGSAS (SEQ ID NO: 26)+LGGC (SEQ ID NO: 27) or GGGC (SEQ ID NO: 28) and the heavy chain was LGGC (SEQ ID NO: 27) or GGGC (SEQ ID NO: 28)+ GGGGS (SEQ ID NO: 25) or GGGGSAS (SEQ ID NO: 26). The expression level was detected and the binding between the antibody and human CD47 or human PD-L1 was detected by ELISA. The results are shown in FIG. 3 and FIG. 4 (wherein 4A represents the ELISA detection result of the bivalent bispecific antibody with B structure, and 4B represents the ELISA detection result of the bivalent bispecific antibody with FV structure). B2 structure performs the best in the expression, assembly and antigen binding among the bispecific antibodies with B-type structure; and FV1 structure performs the best in the expression, assembly and antigen binding among the bispecific antibodies with FV-type structure. Therefore, B2 and FV1 are preferred antibodies.

293E cells were used to perform amplified transient transfection expression of B2 and FV1 structures in Freestyle medium. 24 hours before transfection, 300 mL of 293E cells at $0.5 \times 10^6$ cells/mL were seeded in a 1 L cell culture flask, and cultured in a 37° C., 5% $CO_2$ incubator with shaking at 120 rpm. During transfection, 300 µL of 293fectin™ was added to 5.7 mL Opti-MEM™. After mixing well, the mixture was incubated at room temperature for 2 minutes. Meanwhile, 300 µg of the expression plasmids for B2 and FV1 were diluted to 6 mL with Opti-MEM™, respectively. The diluted transfection reagent 293 fectin and plasmids were mixed thoroughly and incubated at room temperature for 15 minutes. After that, the mixture was added to cells and mixed well, and cultured in a 37° C., 5% $CO_2$ incubator with shaking at 120 rpm for 7 days.

Example 2 Purification and Detection of Preferred Antibodies

Purification of Proteins with B2 Structure

Figure 5:
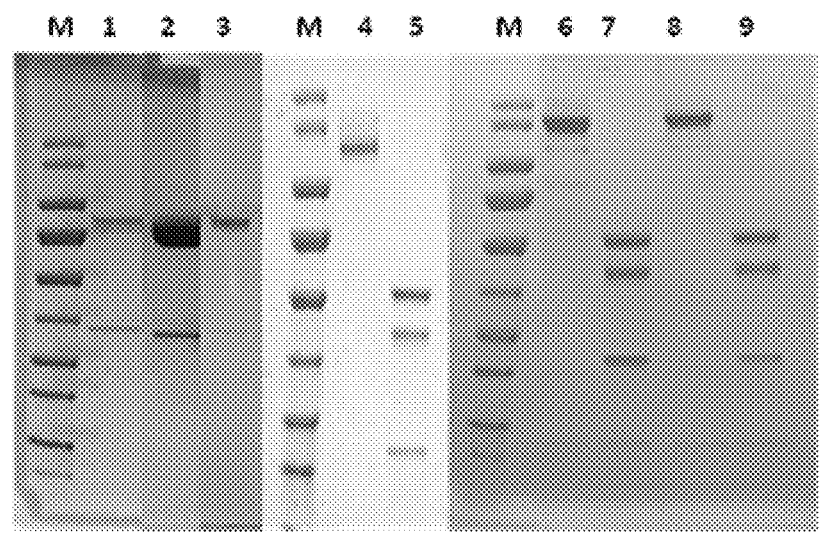
FIG. 5 shows the SDS-PAGE results of the purified bispecific antibodies with preferred B2 structure and with preferred FV1 structure. M indicates Marker; Lanes 1, 2, and 3 represent the supernatants from the non-reducing transient expression of B2 bispecific antibody, the non-reducing eluent of B2 bispecific antibody by Protein L affinity chromatography, and the non-reducing eluent of B2 bispecific antibody by PD-L1 affinity chromatography; Lanes 4, 6, 8 represent the non-reducing eluent of FV1 bispecific antibody by Mab SelectSure affinity chromatography, the non-reducing eluent of FV1 bispecific antibody by Protein L affinity chromatography, and the non-reducing eluent of FV1 bispecific antibody by hCD47 affinity chromatography; and Lanes 5, 7, and 9 represent the reducing eluent of FV1 bispecific antibody by Mab SelectSure affinity chromatography, the reducing eluent of FV1 bispecific antibody by Protein L affinity chromatography, and the reducing eluent of FV1 bispecific antibody by hCD47 affinity chromatography.

The cell culture medium was centrifuged at 2000 g for 20 min, and the supernatant was collected and then filtered with a 0.22 micron filter membrane. Next, the supernatant was subjected to Protein L (GE) chromatography, the proteins were eluted with 20 mM citrate-sodium citrate, pH 3.0, and then the resultant was adjusted to neutral pH with 1 M Tris base. After protein L chromatography, the sample was then subjected to affinity chromatography coupled with human PDL1 protein, the proteins were eluted with 20 mM citrate-sodium citrate, pH 3.0, and then the resultant was adjusted to neutral pH with 1 M Tris base. Purified samples were separated by SDS-PAGE using 4-20% gradient gel (GenScript Biotechnology Co., Ltd.) to detect purified proteins. The results are shown in FIG. 5 and the purity of the preferred antibody B2 was 95%.

Purification of Proteins with FV1 Structure

The cell culture medium was centrifuged at 2000 g for 20 min, and the supernatant was collected and then filtered with a 0.22 micron filter membrane. Next, the supernatant was subjected to Mabselect Sure (GE) chromatography, the proteins were eluted with 20 mM citrate-sodium citrate, pH 3.0, and then the resultant was adjusted to neutral pH with 1 M Tris base. After Mabselect Sure chromatography, the sample was then subjected to Protein L (GE) chromatography, the proteins were eluted with 20 mM citrate-sodium citrate, pH 3.0, and then the resultant was adjusted to neutral pH with 1 M Tris base. After protein L chromatography, the sample was then subjected to affinity chromatography coupled with human CD47 protein, the proteins were eluted with 20 mM citrate-sodium citrate, pH 3.0, and then the resultant was adjusted to neutral pH with 1 M Tris base. Purified samples were separated by SDS-PAGE using 4-20% gradient gel (GenScript Biotechnology Co., Ltd.) to detect purified proteins. The results are shown in FIG. 5 and the purity of the preferred FV1 was 90.8%.

Example 3 ELISA Detection of Preferred Antibodies Binding to Human CD47 and Human PD-L1

1. Coating the first antigen: Human PD-L1-mFc (constructed by GeneScience, SEQ ID NO: 22) was diluted with PBS to 1 µg/mL, and then added to a 96-well microtiter plate at 50 µL per well and incubated overnight at 4° C.

2. Blocking: After being washed three times, the plate was blocked with 3% BSA at 250 µL per well, and incubated at 37° C. for 2 hours.

3. Adding candidate antibody: After washing three times, the candidate antibody was added to the plate, each with 12 samples diluted at a 2-fold concentration gradient with an initial concentration of 10 mg/mL, positive control or negative control was added at 50 µL per well, and incubated at 25° C. for 1 hour.

4. Adding the second antigen: Human CD47-His (constructed by GeneScience, SEQ ID NO: 23) was diluted with PBS to 10 µg/mL, and then added to the 96-well microtiter plate at 50 µL per well and incubated at 25° C. for 1 hour.

5. Adding the secondary antibody: After washing three times, HRP-labeled streptavidin (1:10,000) was added to the plate at 50 µL per well, and incubated at 25° C. for 1 hour.

6. Color development: After being washed four times, TMB color development solution was added to the plate 50 µL per well, and developed color shielded from light at room temperature for 10 minutes.

7. Terminating: The stop solution was directly added to the plate at 50 µL per well to terminate the reaction.

Figure 6:
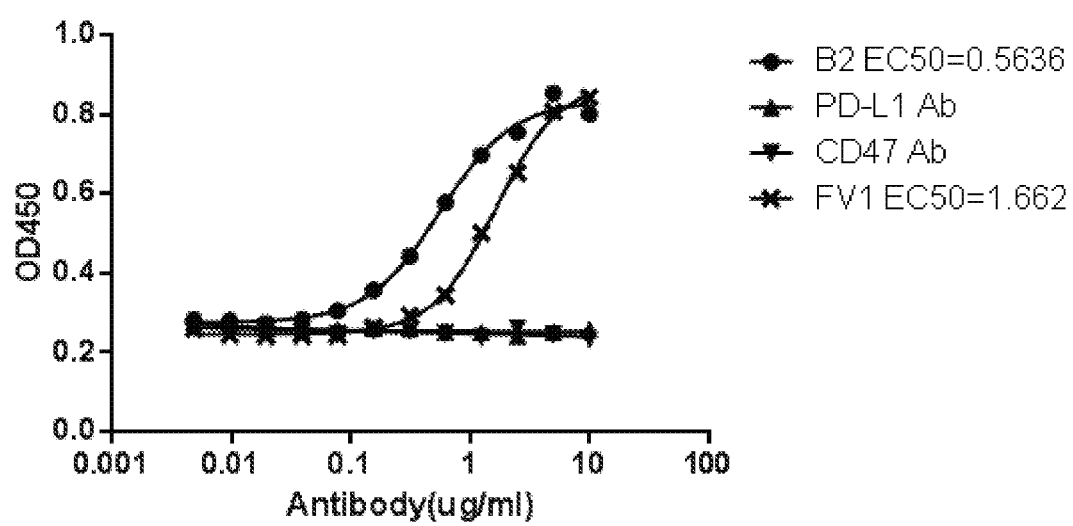
FIG. 6 shows the ELISA results of the bivalent bispecific antibodies with preferred B2 structure and with FV1 structure after purification.

8. Detection: After terminating the reaction, the microtiter plate was immediately put into the microplate reader. The OD value at 450 nm was measured, and the original data was saved for sorting. The results are shown in FIG. 6, showing that for the purified antibody B2, EC50-0.5636; for FV1, EC50=1.662.

Example 4 Affinity Determination of Preferred Antibodies

The affinities of antibodies with B2 structure and with FV1 structure were detected by Biacore T200 instrument. The specific protocols were as follows. Human PD-L1-His and human CD47-His were coupled to CM5 biosensor chip (GE), and then the antibodies of different concentrations were flowed through the chip at a flow rate of 30 μL/min. The binding between the candidate antibody and antigen was performed with a binding time of 120 s and a dissociation time of 300 s. The kinetic fitting was performed using BIAevalution software (GE), and the results of affinity constants were obtained as shown in Table 2 and Table 3. The affinities of B2 and FV1 with PD-L1 were 1.09E-10 M and 2.71E-10 M, respectively; and the affinities of B2 and FV1 with CD47 were 2.58E-8 M and 1.50E-8 M, respectively.

TABLE 2

Results of affinity determination of candidate antibodies with PD-L1

| Antibody | Ka (1/Ms) | Kd (1/s) | KD (M) | Rmax (RU) |
|---|---|---|---|---|
| B2 | 3.95E+05 | 4.28E−05 | 1.09E−10 | 7.067 |
| FV1 | 4.40E+05 | 1.19E−04 | 2.71E−10 | 28.06 |
| PD-L1 positive monoclonal antibody | 9.08E+05 | 2.36E−04 | 2.60E−10 | 80 |

TABLE 3

Results of affinity determination of candidate antibodies with CD47

| Antibody | KD (M) | Rmax (RU) |
|---|---|---|
| B2 | 2.58E−08 | 50.00 |
| FV1 | 1.50E−08 | 60.00 |
| CD47 positive monoclonal antibody | 2.36E−08 | 50.92 |

The foregoing is preferred embodiments of the present disclosure, however, it should be noted that some improvements and modifications can be made thereto by those ordinary skilled in the art without departing from the principles of the present disclosure, and these improvements and modifications should also be deemed to be within the protection scope of the present disclosure.

The invention claimed is:

1. A bivalent bispecific antibody, comprising
   a1) scFv2 that is a single-chain variable fragment (scFv) derived from an antibody that specifically binds to a first antigen, a flexible peptide, a heavy chain constant region CH1 and a partial hinge region of IgG1 in an order of CH1-partial hinge-flexible peptide scFv2, and
   b1) scFv1 that is a single-chain variable fragment (scFv) derived from an antibody that specifically binds to a second antigen and a light chain constant region CL in an order of scFv1-CL; or
   a2) scFv2 that is a single-chain variable fragment specifically binding to a first antigen, a flexible peptide, a heavy chain constant region CH1 and a partial hinge region of IgG1 in an order of scFv2-flexible peptide-CH1-partial hinge, and
   b2) scFv1 that is a single-chain variable fragment specifically binding to a second antigen and a light chain constant region CL in an order of CL-scFv1;
   wherein the order is from N-terminal to C-terminal.

2. The bivalent bispecific antibody according to claim 1, wherein the flexible peptide comprises a sequence of (GGGGS (SEQ ID NO: 25))$_n$ or (GGGGSAS (SEQ ID NO: 26))$_n$, wherein n is an integer greater than 0, and the IgG1 partial hinge region linked to the flexible peptide comprises a sequence of EPKSCDK (SEQ ID NO: 24).

3. The bivalent bispecific antibody according to claim 1, wherein CL and CH1 form a heterodimer via a disulfide bond formed between the terminal cysteine residue in CL and the cysteine residue in the heavy chain hinge region.

4. The bivalent bispecific antibody according to claim 1, where in the bivalent bispecific antibody comprises two chains,
 1) one chain has an amino acid sequence as shown in SEQ ID NO: 2, and
 the other chain has an amino acid sequence as shown in SEQ ID NO: 11;
 2) one chain has an amino acid sequence as shown in SEQ ID NO: 1, and the other chain has an amino acid sequence as shown in SEQ ID NO: 10;
 3) one chain has an amino acid sequence as shown in SEQ ID NO: 3, and the other chain has an amino acid sequence as shown in SEQ ID NO: 12; or
 4) one chain has an amino acid sequence as shown in SEQ ID NO: 4, and the other chain has an amino acid sequence as shown in SEQ ID NO: 13.

5. A method for producing the bivalent bispecific antibody according to claim 1, comprising
 a) transforming a host cell with
  a first vector, comprising a nucleic acid encoding a scFv specifically binding to a first antigen, a flexible peptide, a heavy chain constant region CH1 and a partial hinge region of IgG1, and
  a second vector, comprising a nucleic acid encoding a scFv specifically binding to a second antigen and a light chain constant region CL;
 b) culturing the host cell under conditions that allow the synthesis of an antibody; and
 c) recovering the antibody from the culture.

6. A nucleic acid molecule encoding the bivalent bispecific antibody of claim 1.

7. A host cell, comprising a nucleic acid molecule encoding the bivalent bispecific antibody of claim 1.

8. A composition comprising the bivalent bispecific antibody of claim 1, wherein the composition is a pharmaceutical composition or a diagnostic composition.

* * * * *